(12) United States Patent
Bouchet et al.

(10) Patent No.: US 7,812,180 B2
(45) Date of Patent: Oct. 12, 2010

(54) ELECTROPOLYMERISABLE MONOMERS THAT ARE SOLUBLE IN AQUEOUS SOLUTION AND ELECTROACTIVE PROBES THAT CAN BE OBTAINED WITH SUCH MONOMERS

(75) Inventors: Aurelie Bouchet, Marcilly le Chatel (FR); Carole Chaix, Chaponnay (FR); Bernard Mandrand, Villeurbanne (FR)

(73) Assignees: Biomerieux, Marcy L'Etoile (FR); Centre National de la Recherche Scientifique, Paris (FR)

( * ) Notice: Subject to any disclaimer, the term of this patent is extended or adjusted under 35 U.S.C. 154(b) by 165 days.

(21) Appl. No.: 11/988,655

(22) PCT Filed: Jul. 7, 2006

(86) PCT No.: PCT/FR2006/001640

§ 371 (c)(1), (2), (4) Date: Jan. 11, 2008

(87) PCT Pub. No.: WO2007/006944

PCT Pub. Date: Jan. 18, 2007

(65) Prior Publication Data

US 2009/0053826 A1  Feb. 26, 2009

(30) Foreign Application Priority Data

Jul. 11, 2005  (FR) .................................. 05 52139

(51) Int. Cl.
*C07D 207/00* (2006.01)
(52) U.S. Cl. ........................................ 548/566; 548/413
(58) Field of Classification Search ................. 548/566, 548/413
See application file for complete search history.

(56) References Cited

U.S. PATENT DOCUMENTS

| | | | |
|---|---|---|---|
| 4,769,427 | A | 9/1988 | Nowakowsky et al. |
| 6,197,921 | B1 | 3/2001 | Tan et al. |
| 7,034,164 | B1 | 4/2006 | Cosnier |
| 2003/0099684 | A1 | 5/2003 | Domb |
| 2004/0209252 | A1 | 10/2004 | Garnier |
| 2005/0038234 | A1* | 2/2005 | Chaix-Bauvais et al. .... 530/402 |
| 2006/0189555 | A1 | 8/2006 | Mandrand et al. |

FOREIGN PATENT DOCUMENTS

| | | |
|---|---|---|
| EP | 0 445 619 A2 | 9/1991 |
| FR | 2 005 458 | 12/1969 |
| FR | 2 798 145 | 3/2001 |
| FR | 2 849 038 | 6/2004 |
| WO | WO 95/29199 | 11/1995 |
| WO | WO 96/19967 | 7/1996 |
| WO | WO 01/12699 A1 | 2/2001 |
| WO | WO 01/81446 A1 | 11/2001 |
| WO | WO 02/34796 A1 | 5/2002 |
| WO | WO 03/068787 A1 | 8/2003 |
| WO | WO 2004/037422 A1 | 5/2004 |

OTHER PUBLICATIONS

Lindner et al., Journal of Organometallic Chemistry, 2001, 630:266-274.*
H. Korri-Youssoufi et al. "Electrochemical biosensing of DNA hybridization by electroactive ferrocene functionalized polypyrrole." *Synthetic Metals*, 2001. vol. 119, pp. 265-266.
A.O. Porto et al. "X-ray absorption spectroscopy of iron-doped conducting polymers." *Synthetic Metals*, 1999. vol. 104, pp. 89-94.
H. Korri-Youssoufi et al. "Electrochemical Probing of DNA Based on Oligonucleotide-Functionalized Polypyrrole." *Biomacromolecules*, 2001. vol. 2, pp. 58-64.
Masumi Asakawa et al. "Cyclobis(paraquat-4,4'-biphenylene)—An Organic Molecular Square." *Chem. Eur. J.*, 1996. vol. 2, No. 7, pp. 877-893.
Ekkehard Lindner et al. "Preparation, properties, and reactions of metal-containing heterocycles—Part CV. Synthesis and Structure of polyoxadiphosphaplatinaferrocenophanes." *Journal of Organometallic Chemistry*, 2001. vol. 630, pp. 266-274.
H. Korri-Youssoufi et al. "Toward Bioelectronics: Specific DNA Recognition Based on an Oligonucleotide-Functionalized Polypyrrole." *J. Am. Chem. Soc.*, 1997. vol. 119, pp. 7388-7389.
Saïd Sadki et al. "The mechanisms of pyrrole electropolymerization." *Chem. Soc. Rev.*, 2000. vol. 29, pp. 283-293.
Dave R. van Staveren et al. "Bioorganometallic Chemistry of Ferrocene." *Chem. Rev.*, 2004. vol. 104, pp. 5931-5985.

* cited by examiner

*Primary Examiner*—Rei-tsang Shiao
(74) *Attorney, Agent, or Firm*—Oliff & Berridge, PLC

(57) ABSTRACT

The invention relates to an electropolymerizable monomer, intended to be polymerized in aqueous solution, comprising a single electropolymerizable unit and an electron-donating group, characterized in that it also comprises at least one arm ionizable in aqueous solution. The invention also relates to the polymerization process, to the electroactive probe thus obtained and to the method for the detection of a target ligand in a biological sample.

14 Claims, 8 Drawing Sheets

Figure 1:
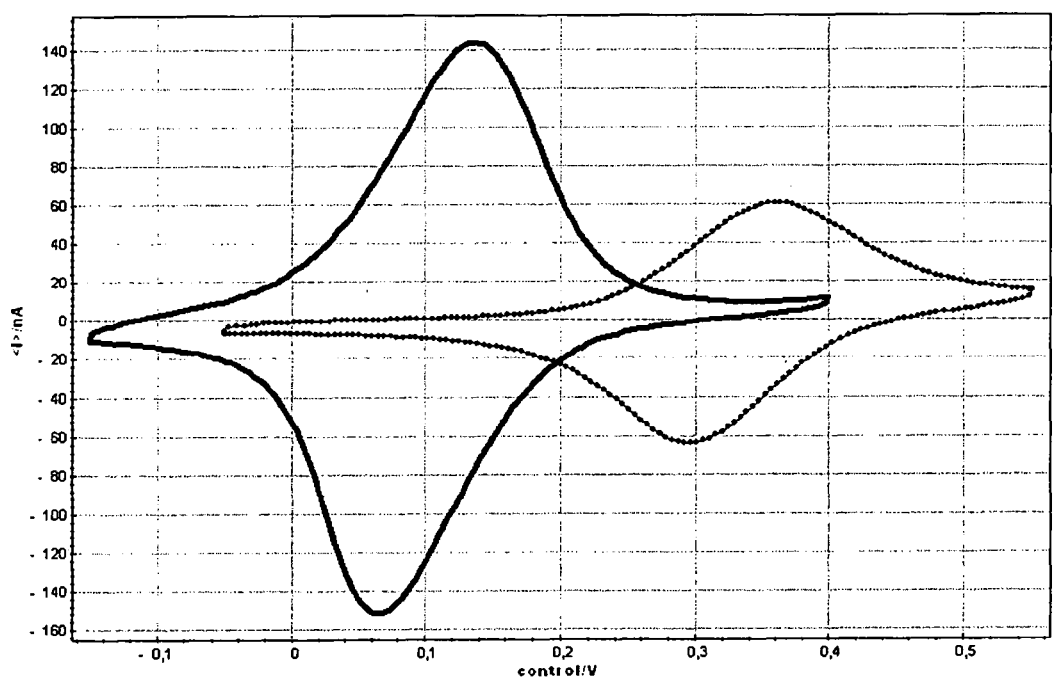

```
                         SEQUENCE LISTING

<160> NUMBER OF SEQ ID NOS: 5

<210> SEQ ID NO 1
<211> LENGTH: 22
<212> TYPE: DNA
<213> ORGANISM: Human immunodeficiency virus

<400> SEQUENCE: 1
gagaccatca atgaggaagc tg                                              22

<210> SEQ ID NO 2
<211> LENGTH: 22
<212> TYPE: DNA
<213> ORGANISM: Hepatitis B virus

<400> SEQUENCE: 2
atctcgggaa tctcaatgtt ag                                              22

<210> SEQ ID NO 3
<211> LENGTH: 22
<212> TYPE: DNA
<213> ORGANISM: Hepatitis B virus

<400> SEQUENCE: 3
gtattccttg gactcataag gt                                              22

<210> SEQ ID NO 4
<211> LENGTH: 33
<212> TYPE: DNA
<213> ORGANISM: Human immunodeficiency virus

<400> SEQUENCE: 4
atcccattct gcagcttcct cattgatggt ctc                                  33

<210> SEQ ID NO 5
<211> LENGTH: 86
<212> TYPE: DNA
<213> ORGANISM: Hepatitis B virus

<400> SEQUENCE: 5
cccagtaaag ttccccacct tatgagtcca aggaattact aacattgaga ttcccgagat     60
tgagatctcg ggaatctcaa tgttag                                          86
```

ELECTROPOLYMERISABLE MONOMERS THAT ARE SOLUBLE IN AQUEOUS SOLUTION AND ELECTROACTIVE PROBES THAT CAN BE OBTAINED WITH SUCH MONOMERS

The invention relates to the technical field of electropolymerization. In particular, a subject matter of the present invention is electropolymerizable monomers which are soluble in aqueous solution.

Electroactive polymers are used in numerous fields of application. For example, it is possible to use electroactive polymers to detect the interaction of a probe biological ligand with a target biological ligand. The specific interaction of a probe ligand with a target ligand results in a substantial and selective variation in the electrochemical properties of the electroactive polymer, such as a reduction in the electroactivity of said polymer. This variation, which depends on the concentration of target ligand bound to a probe ligand, is observed, optionally measured and directly correlated with the amount of target ligand bound. One of the essential applications of this technique thus lies in the detection, identification and optionally assaying of a ligand present in a biological sample. The abovementioned variation is of potentiometric type, and corresponds, for example, to a variation in the oxidation potential of the electroactive polymer before and after interaction, or of amperometric type, and corresponds, for example, to a variation in the oxidation or reduction current of the polymer before and after hybridization, determined at a predetermined potential. In order to exactly characterize the electrochemical response of the polymer, the latter must exhibit a high electroactivity. Polymers obtained by electropolymerization, for example in the form of homopolymer or copolymer pyrroles comprising an electron-donating group, such as a ferrocene, making it possible to improve its electroactivity and its conductivity, have thus been developed and described, in particular in patent application WO 01/81446.

Electropolymerization reactions are generally carried out in an organic solvent, the monomers employed being hydrophobic. As regards electrochemical detection, the systems used to date require electropolymerization in an organic solvent as the monomers used, for example ferrocenyl-comprising monomers, are rather hydrophobic (Synthetic Metals, 2001, 119, 265-266). In point of fact, handling operations in an organic medium are not compatible with the use of biomolecules. The latter are not soluble in such media and/or, very often, are denatured therein and their properties are detrimentally affected. In the case of proteins, a loss of the active confirmation is generally observed.

From this observation, two strategies have emerged to date: the first consists in producing, on an electrode chip, several layers of conductive polymers with, starting from the electrode, a polypyrrole layer (deposited in solvent), a layer of pyrrole/pyrrole-ferocene copolymer (deposited in solvent) and finally a layer of pyrrole/pyrrole copolymer covalently bonded to a biomolecule (deposition in aqueous medium). This strategy, referred to as "multilayer" strategy, is described, for example, in FR 2849038. Polymers which can be used in this strategy are, for example, described in WO 95/29199 and in WO 01/81446, which describes polymers exhibiting an improved electroactivity which are obtained by electropolymerization, for example in the form of homopolymer or copolymer of pyrroles comprising an electron-donating group, such as a ferrocene. This "multilayer" strategy is not entirely satisfactory as it is tedious as a result of the use of several organic solvent/aqueous medium transitions with on each occasion the need to rinse the chip several times.

The other strategy is known as postfunctionalization: it consists of the postpolymerization covalent attachment of biomolecules, in aqueous medium, by virtue of reactive functional groups situated on the polymer layer. Reference may in particular be made to Synthetic Metals 1999, 89-94 and to Biomacromolecules 2001, 2, 58-64. This postfunctionalization strategy does not make possible, for its part, the targeting of biomolecules. Furthermore, it exhibits a lack of spot-to-spot reproducibility related to the variability in the effectiveness of coupling of the biomolecule to the polymer.

In point of fact, the detection of a biomolecule by the electrochemical route is a promising detection proposition, the main advantage of which is the absence of prior labeling of the biomolecules, which is necessary for detection by fluorescence, for example. Furthermore, the equipment necessary for a measurement of electrochemical potential is not very bulky and hints at high operating practicality.

Due to the disadvantages of the prior art, the inventors intend to provide novel monomers which are fully compatible with an electropolymerization reaction an aqueous medium and which thus make it possible to dispense with the use of an organic solvent. For this reason, the monomers according to the invention are entirely compatible for carrying biological ligands.

In this context, a subject matter of the present invention is first of all an electropolymerizable monomer, intended to be polymerized in aqueous solution, comprising a single electropolymerizable unit and an electron-donating group and also at least one arm ionizable in aqueous solution.

Advantageously, the electropolymerizable monomer as defined above exhibits one or more of the following characteristics:

- it is soluble in distilled water, at least up to a concentration of 1 mM, preferably at least up to a concentration of 10 mM and preferentially at least up to a concentration of 30 mM,
- it comprises, as ionizable arm, a connecting arm ionizable in aqueous solution which provides the bonding between the electropolymerizable unit and the electron-donating group; preferably, the ionizable connecting arm comprises a functional group ionizable in aqueous solution chosen from the functional groups: amine, carboxylic acid and phosphate,
- it comprises a nonionizable free arm which is attached to the electron-donating group exclusively,
- it comprises a free arm which carries a biological ligand chosen from polynucleotides, polypeptides, proteins, antigens, antibodies, haptens, biotin or oligosaccharides; in particular, the biological ligand is a polynucleotide;
- the electropolymerizable unit is chosen from acetylene, pyrroles, thiophenes, indoles, anilines, azines, p-phenylenevinylenes, p-phenylenes, pyrenes, furans, selenophenes, pyridazines, carbazoles, acrylates, methacrylates and their derivatives; preferably, the electropolymerizable unit is a pyrrole, the bonding to the ionizable connecting arm preferably being provided at the 3 position of the pyrrole,
- the electron-donating group is chosen from metallocenes, quinone and their derivatives; preferably, the electron-donating group is a ferrocene.

The monomers according to the invention, because of the presence of an arm ionizable in aqueous solution, will be soluble in aqueous solution, thus allowing them to be polymerized in such aqueous media.

Before describing the invention in more detail, certain terms and expressions used in the context of the present invention will now be defined.

The term "electropolymerizable monomer" is understood to mean a monomer comprising a single electropolymerizable unit, said monomer being capable of reacting by electrochemical polymerization with other monomers to form a polymer. An electropolymerizable unit exhibits an alternation of single bonds and double bonds. Mention may be made, as example of electropolymerizable unit, of acetylene, pyrroles, thiophenes, indoles, anilines, azines, p-phenylenevinylenes, p-phenylenes, pyrenes, furans, selenophenes, pyridazines, carbazoles, acrylates, methacrylates and their derivatives. The monomers comprising a single electropolymerizable unit chosen from acetylene, pyrroles, thiophenes, indoles, anilines, azines, p-phenylenevinylenes, p-phenylenes, pyrenes, furans, selenophenes, pyridazines, carbazoles and their derivatives which result in a conductive polymer will be preferred.

The term "arm ionizable in aqueous solution" is understood to mean a hydrophilic chemical group capable of forming a cation or an anion in aqueous solution. The form ionized in aqueous solution is obtained according to a first embodiment without employing a chemical reaction of hydrolysis or decomposition type. The ionized form is, for example, obtained by exchange of a proton or in the form of an ion pair in solution starting from a salt. Such ionizable arms comprise in particular an amine, polyamine, carboxylic acid (—COOH), phosphate or sulfonate group. In order to enhance the hydrophilic nature of the ionizable arm and thus the solubility of the monomer to which it is attached, this can also comprise a polyether group. An ionizable arm is found in the ionic form when it is placed in an aqueous solution which exhibits a pH of between 5 and 8. Advantageously, the ionizable arm is found in the ionized form in distilled water.

According to a second embodiment, the form ionized in aqueous solution is obtained by chemical reaction. In this case, the ionized monomer is obtained by an alkylation reaction starting from the monomer Ia, IIa or IIIa, according to the following scheme:

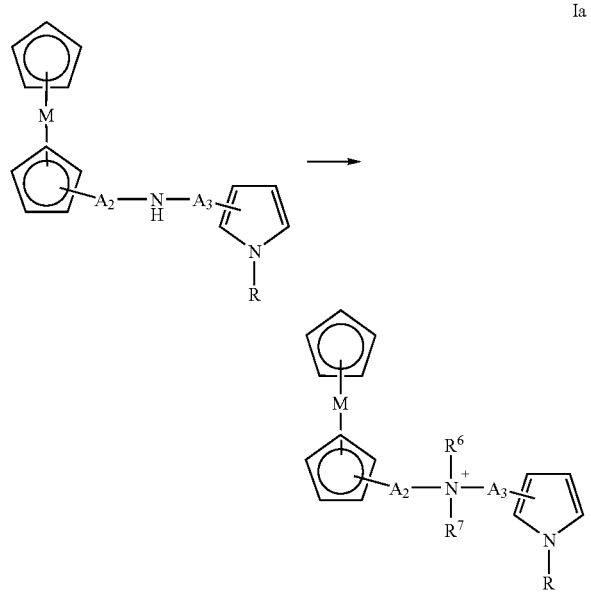

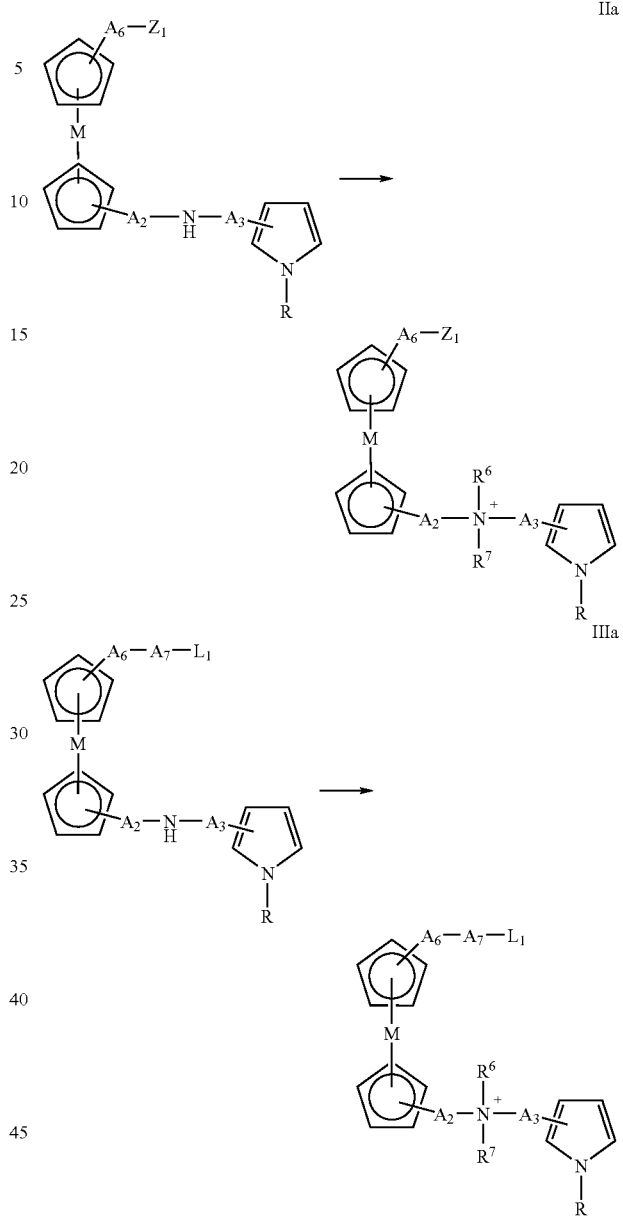

$A_2$, $A_3$, $L_1$, R, $R^6$, $R^7$ and $Z_1$ are as defined below.

Preferably, the alkylation reaction is a bismethylation reaction.

The term "monomer soluble in aqueous solution" is understood to mean a monomer soluble in aqueous solution under the polymerization conditions, namely under the temperature, pH and ionic strength conditions used when it is employed in a polymerization reaction by the electrochemical route. The electropolymerization will generally be carried out in an aqueous solution having a pH of between 3 and 8 and at a temperature of the order of 20 to 30° C. Preferably, the solubility of a monomer according to the invention will be such that the introduction of said monomer into distilled water at a temperature of 25° C., at least up to a concentration of 1 mM, preferably at least up to a concentration of 10 mM, and preferably at least up to a concentration of 30 mM, results in a homogeneous solution which is transparent to the naked eye and which is devoid of precipitation.

The term "polymerization" is understood to mean a reaction by the chemical or electrochemical route of units of the same chemical nature which makes possible the assembling of a certain number of monomers to form a polymer (r'M→(M)$_r$ with r greater than or equal 2). The term "polymerization" encompasses copolymerization and homopolymerization. Advantageously, in the context of the invention, it concerns the condensation of pyrrole units to form a polypyrrole. The term "copolymerization" is understood to mean the simultaneous polymerization of different monomers, such as, for example, the simultaneous polymerization of a mixture of a substituted monomer carrying a biological ligand and of a soluble monomer not comprising a biological ligand.

The terms "electropolymerization", "electrocopolymerization", "electrochemical copolymerization" and "electrochemical polymerization" denote a polymerization by the electrochemical route. Electropolymerization processes are well known to a person skilled in the art. Mention will be made, for example, of the cyclic voltamperometry, chronopotentiometry (applied current) and chronamperometry (applied potential) techniques. In a specific embodiment of the invention, the polymerization will be carried out by a deposition by chronoamperometry or controlled potential deposition. This method consists in imposing a jump in potential from the equilibrium potential (zero current) up to a set value at which the reaction takes place at the electrode and in measuring the current as a function of time.

The "polymerization conditions" denote the pH, the temperature and the ionic strength of the aqueous solution used during the polymerization. In the case of pyrrole, the electropolymerization is carried out by the Diaz mechanism (Sadki et al., *Chem. Soc. Rev.,* 29, 283-293, 2000) and results in the formation of the polypyrrole. This polymerization is carried out at the 2 and 5 positions of the pyrrole monomers. A pyrrole substituted in a 3 or 4 position of the pyrrole nucleus is thus capable of polymerizing or of copolymerizing with other pyrroles at the 2 and 5 positions. Pyrrole units substituted in the 3 position are preferred.

The term "conductor polymer" is understood to mean a polymer having highly delocalized electrons, generally along a sequence of single and double bonds (conjugated bonds), which results in its behaving as a microelectronic semiconductor.

The term "electron-donating group" is understood to mean a chemical group corresponding to a redox pair exhibiting a narrow, rapid and reversible oxidation wave, such as metallocenes, for example ferrocene, quinone and their derivatives.

The protective groups for alcohols, amines and carboxylic acids are well known to a person skilled in the art. Reference may in particular be made to "Protective Groups in Organic Synthesis" 2nd edition, Greene T. W. and Wuts P. G. M., published by John Wiley and Sons, 1991.

Mention may be made, as protected group for alcohols, by way of example, of the acyl, trityl, silyl and tetrahydrofuranyl groups.

Mention may be made, as protective group for carboxylic acids, by way of example, of the chemical groups resulting in esters, in particular alkyl esters, acyl esters, silyl esters or thioesters.

Mention may be made, as protective group for amines, by way of example, of the trifluoroacetyl, tert-butoxycarbonyl and 9-fluorenylmethoxycarbonyl groups.

Mention may be made, as activating group for carboxylic acids, by way of example, of the succinimidyl or phthalimidyl groups or any other group which makes it possible to form an activated ester.

Mention may be made, as activating group for alcohols or amines, by way of example, of the groups resulting, in the case of alcohols, in a phosphodiester, phosphotriester, H-phosphonate or phosphoramidite and, in the case of amines, in a phosphoramidate monoester, phosphoramidate diester, H-phosphoramidate or phosphoramidite. Such groups are chosen in particular from:

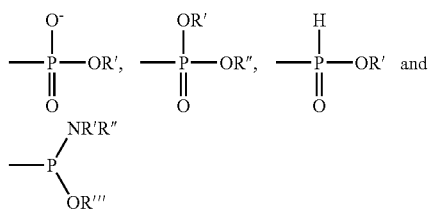

with R', R", R''' which represent an alkyl or aryl group, for example.

The term "biological ligand" is understood to mean a compound which has at least one recognition site which allows it to react with a target molecule of biological interest. Mention may be made, by way of example, as biological ligands, of polynucleotides, antigens, antibodies, polypeptides, proteins, haptens, biotin, oligosaccharides, and the like. A ligand/antiligand pair capable of specifically interacting to form a conjugate is also known, in the present invention, as probe ligand/target ligand.

The term "polynucleotide" means a sequence of at least 2 deoxyribonucleotides or ribonucleotides optionally comprising at least one modified nucleotide, for example at least one nucleotide comprising a modified base, such as inosine, 5-methyldeoxycytidine, 5-(dimethylamino)deoxyuridine, deoxyuridine, 2,6-diaminopurine, 5-bromodeoxyuridine or any other modified base which makes possible hybridization. This polynucleotide can also be modified at the internucleotide bond, such as, for example, phosphorothioates, H-phosphonates, or alkylphosphonates, or in the backbone, such as, for example, alpha-oligonucleotides (FR 2 607 507), or PNA$_S$ (Egholm M. et al., J. Am. Chem., Soc., 1992, 114, 1895-1897), or 2-O-alkylribose, or LNA (Locked Nucleic Acids, described in particular in the patent application published under the number WO 00/66 604). Each of these modifications can be taken in combination. The polynucleotide can be an oligonucleotide, a natural nucleic acid or its fragment, such as a DNA, a ribosomal RNA, a messenger RNA, a transfer RNA, a nucleic acid obtained by an enzymatic amplification technique.

The term "polypeptide" is understood to mean a sequence of at least two amino acids. The term "amino acids" is understood to mean primary amino acids which encode proteins, amino acids derived after enzymatic action, such as trans-4-hydroxyproline, and amino acids which are natural but not present in proteins, such as norvaline, N-methyl-L-leucine or staline (Hunt S. in Chemistry and Biochemistry of the Amino Acids, Barett G. C., published by Chapman and Hall, London, 1985), amino acids protected by chemical functional groups which can be used in synthesis on a solid support or in the liquid phase, and unnatural amino acids.

The term "hapten" denotes nonimmunogenic compounds, that is to say compounds incapable by themselves of promoting an immune reaction by production of antibodies but capable of being recognized by antibodies obtained by immunization of animals under known conditions, in particular by immunization with a hapten-protein conjugate. These compounds generally have a molecular weight of less than 3000 Da and generally of less than 2000 Da and can, for example, be glycosylated peptides, metabolites, vitamins, hormones, prostaglandins, toxins, antibiotics or various medicaments, nucleosides and nucleotides.

The term "antibody" includes polyclonal or monoclonal antibodies, antibodies obtained by genetic recombination and antibody fragments. The term "antigen" denotes a compound capable of being recognized by an antibody, the synthesis of which it has induced by an immune response. The term "protein" includes holoproteins and heteroproteins, such as nucleoproteins, lipoproteins, phosphoproteins, metalloproteins and glycoproteins, both fibrous and globular.

According to another of its aspects, a subject matter of the present invention is the various series of monomers comprising a pyrrole unit and a metallocene unit as defined below:

a) first of all the monomers of formula (I):

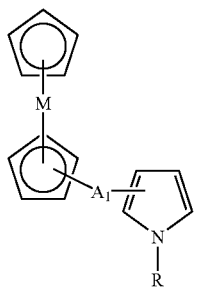

(I)

in which:

M is a transition metal, preferably Fe, Ru or Os, $A_1$ is a sequence:
-$A_2$-X-$A_3$- with:
X which represents —$NR^1$—, —Y—P(O)($OR^2$)—O— or —$N^+R^6R^7$—
Y which represents O or NH,
$A_2$ which represents —$(CH_2)_{m1}$—, —$(CH_2)_{m2}$—O—$[(CH_2)_2O]_{m3}$—$(CH_2)_2$— or —$(CH_2)_{m4}$—C(O)—$NR^3$—$[(CH_2)_2O]_{m5}$—$(CH_2)_2$—
$A_3$ which represents —$(CH_2)_{n1}$—, —$[(CH_2)_2O]_{n2}$—$(CH_2)_{n3}$— or —$[(CH_2)_2O]_{n4}$—$(CH_2)_2$—$NR^4$—C(O)—$(CH_2)_{n5}$—,
m1 and n1 which represent, each independently of one another, an integer included within the range extending from 1 to 6; it being understood that, if X represents —$NR^1$— and the groups $A_2$ and $A_3$ respectively represent —$(CH_2)_{m1}$— and —$(CH_2)_{n1}$—, then the sum m1+n1 is included within the range extending from 2 to 6,
m2 and n3 which represent, each independently of one another, an integer included within the range extending from 0 to 3, preferably within the range extending from 1 to 3,
m3, n2, m4, n4, m5 and n5 which represent, each independently of one another, an integer included within the range extending from 0 to 6, preferably within the range extending from 1 to 6,
$R^1$, $R^3$ and $R^4$ which represent, each independently of one another, a hydrogen atom or a ($C_1$-$C_4$)alkyl group, and $R^2$ which represents a hydrogen atom or a ($C_1$-$C_4$) alkyl, cyanoethyl or 2-chlorophenyl group,
or else -$A_4$-[NH($CH_2$)$_2$]$_n$-$A_5$- with:
$A_4$ which represents —$(CH_2)_{p1}$— or —$(CH_2)_{p2}$—C(O)—,
$A_5$ which represents —$(CH_2)_{q1}$— or —$NR^5$—C(O)—$(CH_2)_{q2}$—,
n which is an integer included within the range extending from 2 to 6,
p1, q1, p2 and q2 which represent, each independently of one another, an integer included within the range extending from 1 to 6,
$R^5$ which represents a hydrogen atom or a ($C_1$-$C_4$) alkyl group, for example methyl or ethyl,
$R^6$, $R^7$ which represent, each independently of one another, a ($C_1$-$C_4$)alkyl group, R represents a hydrogen atom or a protective group for the amine functional group, for example chosen from the monomethoxytrityl, dimethoxytrityl, tosyl, triisopropylsilyl, tert-butoxycarbonyl, 9-fluorenyl-oxycarbonyl, benzyloxycarbonyl, triphenylmethanesulfenyl and acetyl groups, b) subsequently the monomers of formula (II):

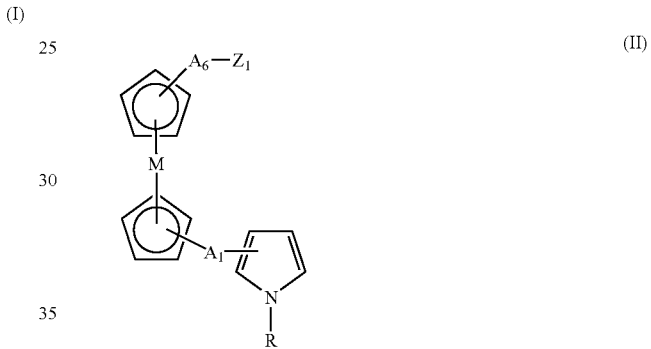

(II)

in which:
M, $A_1$ and R are as defined for the monomers of formula (I),
$A_6$ represents a spacer arm defined as follows:
when $A_1$ is a sequence -$A_2$-$NR^1$-$A_3$- or -$A_2$-$N^+R^6R^7$-$A_3$-, in which $R^1$, $A_2$, $A_3$, $R^6$ and $R^7$ are as defined for the monomers of formula (I), and
when $A_2$ represents —$(CH_2)_{m1}$— or —$(CH_2)_{m2}$—O—$[(CH_2)_2O]_{m3}$—$(CH_2)_2$— and $A_3$ represents —$(CH_2)_{n1}$— or —$[(CH_2)_2O]_{n2}$—$(CH_2)_{n3}$—, then $A_6$ represents a sequence -$A_2$-$NR^1$—, with m1, m2, m3, n1, n2, n3 and $R^1$ as defined for the monomers of formula (I),
when $A_2$ represents —$(CH_2)_{m4}$—C(O)—$NR^3$—$[(CH_2)_2O]_{m5}$—$(CH_2)_2$— and $A_3$ represents —$(CH_2)_{n1}$— or —$[(CH_2)_2O]_{n2}$—$(CH_2)_{n3}$—, then $A_6$ represents a sequence —$(CH_2)_{m4}$—C(O)O— or -$A_2$-$NR^1$—, with m4, $R^3$, m5, n1, n2, n3 and $R^1$ as defined for the monomers of formula (I),
when $A_2$ represents —$(CH_2)_{m1}$— or —$(CH_2)_{m2}$—O—$[(CH_2)_2O]_{m3}$—$(CH_2)_2$— and $A_3$ represents —$[(CH_2)_2O]_{n4}$—$(CH_2)_2$—$NR^4$—C(O)—$(CH_2)_{n5}$—, then $A_6$ represents a sequence -$A_2$-$NR^1$— or -$A_2$-$NR^1$—$[(CH_2)_2O]_{n4}$—$(CH_2)_2$—$NR^4$—, with m1, m2, m3, n4, $R^4$, n5 and $R^1$ as defined for the monomers of formula (I),
when $A_2$ represents —$(CH_2)_{m4}$—C(O)—$NR^3$—$[(CH_2)_2O]_{m5}$—$(CH_2)_2$— and $A_3$ represents —$[(CH_2)_2O]_{n4}$—$(CH_2)_2$—$NR^4$—C(O)—$(CH_2)_{n5}$—, then $A_6$ represents a sequence —(CH$_2$)$_{m4}$—C(O)O—, -A$_2$-NR$^1$— or -A$_2$-NR$^1$—[(CH$_2$)$_2$O]$_{n4}$—(CH$_2$)$_2$—NR$^4$—, with m4, R$^3$, m5, n4, n5, R$^4$ and R$^1$ as defined for the monomers of formula (I), when A$_1$ is a sequence -A$_2$-Y—P(O)(OR$^2$)—O-A$_3$-, in which R$^2$, A$_2$, A$_3$ and Y are as defined for the monomers of formula (I), and when A$_2$ represents —(CH$_2$)$_{m1}$— or —(CH$_2$)$_{m2}$—O—[(CH$_2$)$_2$O]$_{m3}$—(CH$_2$)$_2$— and A$_3$ represents —(CH$_2$)$_{n1}$— or —[(CH$_2$)$_2$O]$_{n2}$—(CH$_2$)$_{n3}$—, then A$_6$ represents a sequence -A$_2$-Y—, with m1, m2, m3, n1, n2, n3 and Y as defined for the monomers of formula (I), when A$_2$ represents —(CH$_2$)$_{m4}$—C(O)—NR$^3$—[(CH$_2$)$_2$O]$_{m5}$—(CH$_2$)$_2$— and A$_3$ represents —(CH$_2$)$_{n1}$— or —[(CH$_2$)$_2$O]$_{n2}$—(CH$_2$)$_{n3}$—, then A$_6$ represents a sequence —(CH$_2$)$_{m4}$—C(O)O— or -A$_2$-Y—, with m4, R$^3$, m5, n1, n2, n3 and Y as defined for the monomers of formula (I), when A$_2$ represents —(CH$_2$)$_{m1}$— or —(CH$_2$)$_{m2}$—O—[(CH$_2$)$_2$O]$_{m3}$—(CH$_2$)$_2$— and A$_3$ represents —[(CH$_2$)$_2$O]$_{n4}$—(CH$_2$)$_2$—NR$^4$—C(O)—(CH$_2$)$_{n5}$—, then A$_6$ represents a sequence -A$_2$-Y— or -A$_2$-Y—P(O)(OR$^2$)—O—[(CH$_2$)$_2$O]$_{n4}$—(CH$_2$)$_2$—NR$^4$—, with m1, m2, m3, n4, n5, Y, R$^4$ and R$^2$ as defined for the monomers of formula (I), when A$_2$ represents —(CH$_2$)$_{m4}$—C(O)—NR$^3$—[(CH$_2$)$_2$O]$_{m5}$—(CH$_2$)$_2$— and A$_3$ represents —[(CH$_2$)$_2$O]$_{n4}$—(CH$_2$)$_2$—NR$^4$—C(O)—(CH$_2$)$_{n5}$—, then A$_6$ represents a sequence —(CH$_2$)$_{m4}$—C(O)O—, -A$_2$-Y— or -A$_2$-Y—P(O)(OR$^2$)—O—[(CH$_2$)$_2$O]$_{n4}$—(CH$_2$)$_2$—NR$^4$—, with m4, R$^3$, m5, n4, n5, R$^2$, R$^4$ and Y as defined for the monomers of formula (I), when A$_1$ is a sequence -A$_4$-[NH(CH$_2$)$_2$]$_n$-A$_5$-, in which A$_4$, n and A$_5$ are as defined for the monomers of formula (I), when A$_4$ represents —(CH$_2$)$_{p2}$—C(O)—, if A$_5$ represents —(CH$_2$)$_{q1}$', then A$_6$ represents a sequence —(CH$_2$)$_{p2}$—C(O)O— or -A$_4$-[NH(CH$_2$)$_2$]$_n$—NH—, and, if A$_5$ represents —NR$^5$—C(O)—(CH$_2$)$_{q2}$—, then A$_6$ represents a sequence —(CH$_2$)$_{p2}$—C(O)O—, -A$_4$-[NH(CH$_2$)$_2$]$_n$—NR$^5$— or -A$_4$-[NH(CH$_2$)$_2$]$_n$—NH—, with p2, R$^5$, q1, q2 and n as defined for the monomers of formula (I) and n' an integer included within the range extending from 1 to n–1, when A$_4$ represents —(CH$_2$)$_{p1}$—, if A$_5$ represents —(CH$_2$)$_{q1}$—, then A$_6$ represents a sequence —(CH$_2$)$_{p1}$—[NH(CH$_2$)$_2$]$_n$—NH—, with n' an integer included within the range extending from 1 to n–1, and, if A$_5$ represents —NR$^5$—C(O)—(CH$_2$)$_{q2}$—, then A$_6$ represents a sequence —(CH$_2$)$_{p1}$—[NH(CH$_2$)$_2$]$_n$—NR$^5$— or —(CH$_2$)$_{p1}$—[NH(CH$_2$)$_2$]$_n$—NH—, with p1, q1, q2, n and R$^5$ as defined for the monomers of formula (I) and n' an integer included within the range extending from 1 to n–1, Z$_1$ represents a hydrogen atom or a protective or activating group for alcohols, amines or carboxylic acids, as a function respectively of the amine, alkoxy or carboxyl end functional group of the spacer arm A$_6$ to which Z$_1$ is bonded, c) and the monomers of formula (III):

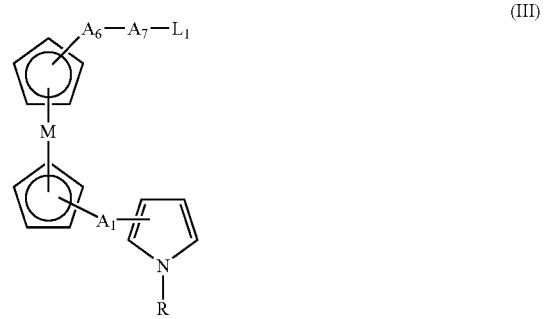

in which:

M, A$_1$ and R are as defined for the monomers of formula (I),

A$_6$ represents a spacer arm defined as follows:

when A$_1$ is a sequence -A$_2$-NR$^1$-A$_3$- or -A$_2$-N$^+$R$^6$R$^7$-A$_3$-, in which R$^1$, A$_2$, A$_3$, R$^6$ and R$^7$ are as defined for the monomers of formula (I), and when A$_2$ represents —(CH$_2$)$_{m1}$— or —(CH$_2$)$_{m2}$—O—[(CH$_2$)$_2$O]$_{m3}$—(CH$_2$)$_2$— and A$_3$ represents —(CH$_2$)$_{n1}$— or —[(CH$_2$)$_2$O]$_{n2}$—(CH$_2$)$_{n3}$—, then A$_6$ represents a sequence -A$_2$-NR$^1$—, with m1, m2, m3, n1, n2, n3 and R$^1$ as defined for the monomers of formula (I), when A$_2$ represents —(CH$_2$)$_{m4}$—C(O)—NR$^3$—[(CH$_2$)$_2$O]$_{m5}$—(CH$_2$)$_2$— and A$_3$ represents —(CH$_2$)$_{n1}$— or —[(CH$_2$)$_2$O]$_{n2}$—(CH$_2$)$_{n3}$—, then A$_6$ represents a sequence —(CH$_2$)$_{m4}$—C(O)O— or -A$_2$-NR$^1$—, with m4, R$^3$, m5, n1, n2, n3 and R$^1$ as defined for the monomers of formula (I), when A$_2$ represents —(CH$_2$)$_{m1}$— or —(CH$_2$)$_{m2}$—O—[(CH$_2$)$_2$O]$_{m3}$—(CH$_2$)$_2$— and A$_3$ represents —[(CH$_2$)$_2$O]$_{n4}$—(CH$_2$)$_2$—NR$^4$—C(O)—(CH$_2$)$_{n5}$—, then A$_6$ represents a sequence -A$_2$-NR$^1$— or -A$_2$-NR$^1$—[(CH$_2$)$_2$O]$_{n4}$—(CH$_2$)$_2$—NR$^4$—, with m1, m2, m3, n4, n5, R$^4$ and R$^1$ as defined for the monomers of formula (I), when A$_2$ represents —(CH$_2$)$_{m4}$—C(O)—NR$^3$—[(CH$_2$)$_2$O]$_{m5}$—(CH$_2$)$_2$— and A$_3$ represents —[(CH$_2$)$_2$O]$_{n4}$—(CH$_2$)$_2$—NR$^4$—C(O)—(CH$_2$)$_{n5}$—, then A$_6$ represents a sequence —(CH$_2$)$_{m4}$—C(O)O—, -A$_2$-NR$^1$— or -A$_2$-NR$^1$—[(CH$_2$)$_2$O]$_{n4}$—(CH$_2$)$_2$—NR$^4$—, with m4, R$^3$, m5, n4, n5, R$^4$ and R$^1$ as defined for the monomers of formula (I), when A$_1$ is a sequence -A$_2$-Y—P(O)(OR$^2$)—O-A$_3$-, in which R$^2$, A$_2$, A$_3$ and Y are as defined for the monomers of formula (I), and when A$_2$ represents —(CH$_2$)$_{m1}$— or —(CH$_2$)$_{m2}$—O—[(CH$_2$)$_2$O]$_{m3}$—(CH$_2$)$_2$— and A$_3$ represents —(CH$_2$)$_{n1}$— or —[(CH$_2$)$_2$O]$_{n2}$—(CH$_2$)$_{n3}$—, then A$_6$ represents a sequence -A$_2$-Y—, with m1, m2, m3, n1, n2, n3 and Y as defined for the monomers of formula (I), when A$_2$ represents (CH$_2$)$_{m4}$—C(O)—NR$^3$—[(CH$_2$)$_2$O]$_{m5}$—(CH$_2$)$_2$— and A$_3$ represents —(CH$_2$)$_{n1}$— or —[(CH$_2$)$_2$O]$_{n2}$—(CH$_2$)$_{n3}$—, then A$_6$ represents a sequence —(CH$_2$)$_{m4}$—C(O)O— or -A$_2$-Y—, with m4, R$^3$, m5, n1, n2, n3 and Y as defined for the monomers of formula (I), when A$_2$ represents —(CH$_2$)$_{m1}$— or —(CH$_2$)$_{m2}$—O—[(CH$_2$)$_2$O]$_{m3}$—(CH$_2$)$_2$— and A$_3$ represents —[(CH$_2$)$_2$O]$_{n4}$—(CH$_2$)$_2$—NR$^4$—C(O)—(CH$_2$)$_{n5}$—, then A$_6$ represents a sequence -A$_2$-Y— or -A$_2$-Y—P(O)(OR$^2$)—O—[(CH$_2$)$_2$O]$_{n4}$—(CH$_2$)$_2$—NR$^4$—, with m1, m2, m3, n4, n5, Y, R$^4$ and R$^2$ as defined for the monomers of formula (I), when A$_2$ represents —(CH$_2$)$_{m4}$—C(O)—NR$^3$—[(CH$_2$)$_2$O]$_{m5}$—(CH$_2$)$_2$— and A$_3$ represents —[(CH$_2$)$_2$O]$_{n4}$—(CH$_2$)$_2$—NR$^4$—C(O)—(CH$_2$)$_{n5}$—, then A$_6$ represents a sequence —(CH$_2$)$_{m4}$—C(O)O—, -A$_2$-Y— or -A$_2$-Y—P(O)(OR$^2$)—O—[(CH$_2$)$_2$O]$_{n4}$—(CH$_2$)$_2$—NR$^4$—, with m4, R$^3$, m5, n4, n5, R$^2$, R$^4$ and Y as defined for the monomers of formula (I), when A$_1$ is a sequence -A$_4$-[NH(CH$_2$)$_2$]$_n$-A$_5$-, in which A$_4$, n and A$_5$ are as defined for the monomers of formula (I), when A$_4$ represents —(CH$_2$)$_{p2}$—C(O)—, if A$_5$ represents —(CH$_2$)$_{q1}$—, then A$_6$ represents a sequence —(CH$_2$)$_{p2}$—C(O)O— or -A$_4$-[NH(CH$_2$)$_2$]$_n$—NH—, and, if A$_5$ represents —NR$^5$—C(O)—(CH$_2$)$_{q2}$—, then A$_6$ represents a sequence —(CH$_2$)$_{p2}$—C(O)O—, -A$_4$-[NH(CH$_2$)$_2$]$_n$—NR$^5$— or -A$_4$-[NH(CH$_2$)$_2$]$_n$—NH—, with p2, R$^5$, q1, q2 and n as defined for the monomers of formula (I) and n' an integer included within the range extending from 1 to n−1, when A$_4$ represents —(CH$_2$)$_{p1}$—, if A$_5$ represents —(CH$_2$)$_{q1}$—, then A$_6$ represents a sequence —(CH$_2$)$_{p1}$—[NH(CH$_2$)$_2$]$_n$—NH— with n' an integer included within the range extending from 1 to n−1, and, if A$_5$ represents —NR$^5$—C(O)—(CH$_2$)$_{q2}$—, then A$_6$ represents a sequence —(CH$_2$)$_{p1}$—[NH(CH$_2$)$_2$]$_n$—NR$^5$— or -A$_4$-(CH$_2$)$_{p1}$—[NH(CH$_2$)$_2$]$_n$—NH—, with p1, q1, q2, n and R$^5$ as defined for the monomers of formula (I) and n' an integer included within the range extending from 1 to n−1, A$_7$ represents a connecting arm, such as a polymer or an alkyl chain, or a direct bond, and L$_1$ represents a biological ligand.

The ionizable arms (connecting or free) present on these monomers make it possible to obtain a monomer soluble in aqueous solution, despite the presence of a metallocene group, typically a ferrocene group, possessing a hydrophobic nature. Furthermore, the presence of this ionizable arm does not in any way detrimentally affect the properties of the electropolymerizable monomer present, it being possible for the polymerization to be carried out in aqueous phase to form polymer layers which will preferably be conducting.

It should be emphasized that, in the compounds of formulae (II) and (III), the sequence A$_6$ corresponds partially to the arm A$_1$; this is why the value which A$_6$ takes is directly related to the value of A$_2$ and A$_3$ in particular.

In order not to overload the definition of the arms A$_6$ in the monomers (II) and (III), although it is specified at each point to what A$_2$ corresponds, the name A$_2$ has been retained to define A$_6$. For example, even though it is specified that A$_2$ represents —(CH$_2$)$_{m4}$—C(O)—NR$^3$—[(CH$_2$)$_2$O]$_{m5}$—(CH$_2$)$_2$—, the definition -A$_2$-Y— will have been retained for A$_6$, whereas, of course, this corresponds to —(CH$_2$)$_{m4}$—C(O)—NR$^3$—[(CH$_2$)$_2$O]$_{m5}$—(CH$_2$)$_2$—Y. It is the same for A$_4$.

Among the monomers of formula (I), the monomers of formulae (Ia), (Ib) and (Ic) as defined below are preferred.

The monomers (Ia) correspond to the following formula (Ia):

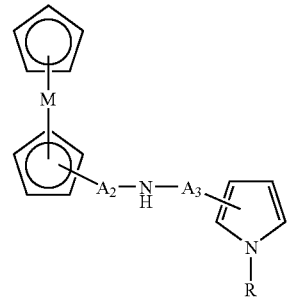

(Ia)

with M, A$_2$, A$_3$ and R as defined for the monomers of formula (I), it being understood that at least one of the sequences A$_2$ and A$_3$ comprises a unit —[(CH$_2$)$_2$O]$_m$— with m which represents m3, m5, n2 or n4 as defined for the monomers of formula (I). Preference is given to the monomers of formula (Ia) as defined above in which A$_2$ represents —(CH$_2$)$_{m1}$— and A$_3$ represents —[(CH$_2$)$_2$O]$_{n4}$—(CH$_2$)$_2$—NR$^4$—C(O)—(CH$_2$)$_{n5}$—, with m1, n4, n5 and R$^4$ as defined for the monomers of formula (I) and in particular m1=1, n4=2, n5=1 and R$^4$=H. The monomers (Ic) correspond to the following formula (Ic):

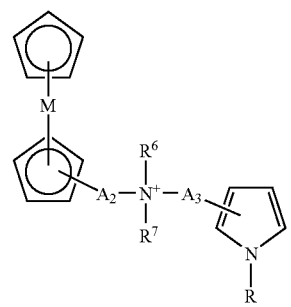

with M, A$_2$, A$_3$ R, R$^6$ and R$^7$ as defined for the monomers of formula (I), it being understood that at least one of the sequences A$_2$ and A$_3$ comprises a unit —[(CH$_2$)$_2$O]$_m$— with m which represents m3, m5, n2 or n4 as defined for the monomers of formula (I). Preference is given to the monomers of formula (Ic) as defined above in which A$_2$ represents —(CH$_2$)$_{m1}$— and A$_3$ represents —[(CH$_2$)$_2$O]$_{n4}$—(CH$_2$)$_2$—NR$^4$—C(O)—(CH$_2$)$_{n5}$—, with m1, n4, n5 and R$^4$ as defined for the monomers of formula (I) and in particular m1=1, n4=2, n5=1 and R$^4$=H.

The monomers (Ib) correspond to the following formula (Ib):

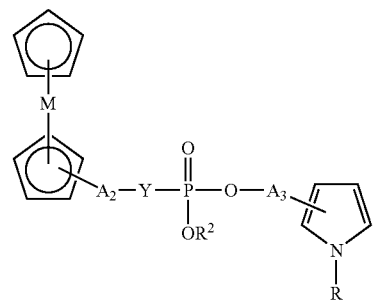

(Ib)

with M, A$_2$, A$_3$, R$^2$ and R as defined for the monomers of formula (I). Advantageously, the monomers (Ib) exhibit one or more of the following characteristics:

Y=O;

R² represents a hydrogen atom;

A₂ and A₃ respectively represent —(CH₂)$_{m1}$— and —(CH₂)$_{n1}$—, with m1 and n1 as defined for the monomers of formula (I) and in particular m1=3 and n1=2.

Likewise, among the monomers of formula (II), the monomers of formulae (IIa), (IIc) and (IIb) as defined below are preferred. These monomers of formulae (II), (IIa), (IIc) and (IIb) respectively correspond to the monomers of formulae (I), (Ia), (Ic) and (Ib) modified to carry, on the other cyclopentadiene of the metallocene, an ionizable free arm. The latter can carry a reactive functional group (F) of amine, hydroxyl or carboxylic acid type, optionally in the protected or activated form, for the subsequent attachment of a biological ligand in particular.

The monomers (IIa) correspond to the following formula (IIa):

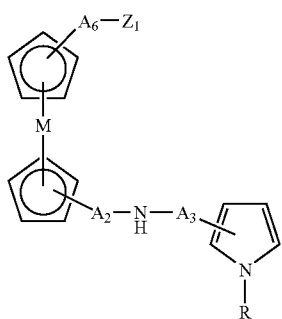

in which:

M and R are as defined for the monomers of formula (I),

A₂ represents —(CH₂)$_{m1}$—, —(CH₂)$_{m2}$—O—[(CH₂)₂O]$_{m3}$—(CH₂)₂— or —(CH₂)$_{m4}$—C(O)—NR³—[(CH₂)₂O]$_{m5}$—(CH₂)₂—, with m1 to m5 and R³ as defined for the monomers of formula (I), A₃ represents —(CH₂)$_{n1}$—, —[(CH₂)₂O]$_{n2}$—(CH₂)$_{n3}$— or —[(CH₂)₂O]$_{n4}$—(CH₂)₂—NR⁴—C(O)—(CH₂)$_{n5}$—, with n1 to n5 and R⁴ as defined for the monomers of formula (I), A₆ represents a spacer arm defined as follows:

when A₂ represents —(CH₂)$_{m1}$— or —(CH₂)$_{m2}$—O—[(CH₂)₂O]$_{m3}$—(CH₂)₂— and A₃ represents —(CH₂)$_{n1}$— or —[(CH₂)₂O]$_{n2}$—(CH₂)$_{n3}$—, then A₆ represents a sequence -A₂-NH—, with m1, m2, m3, n1, n2 and n3 as defined for the monomers of formula (I), when A₂ represents —(CH₂)$_{m4}$—C(O)—NR³—[(CH₂)₂O]$_{m5}$—(CH₂)₂— and A₃ represents —(CH₂)$_{n1}$— or —[(CH₂)₂O]$_{n2}$—(CH₂)$_{n3}$—, then A₆ represents a sequence —(CH₂)$_{m4}$—C(O)O— or -A₂-NH—, with m4, R³, m5, n1, n2 and n3 as defined for the monomers of formula (I), when A₂ represents —(CH₂)$_{m1}$— or —(CH₂)$_{m2}$—O—[(CH₂)₂O]$_{m3}$—(CH₂)₂— and A₃ represents —[(CH₂)₂O]$_{n4}$—(CH₂)₂—NR⁴—C(O)—(CH₂)$_{n5}$—, then A₆ represents a sequence -A₂-NH— or -A₂-NH—[(CH₂)₂O]$_{n4}$—(CH₂)₂—NR⁴—, with m1, m2, m3, n4, R⁴ and n5 as defined for the monomers of formula (I), when A₂ represents —(CH₂)$_{m4}$—C(O)—NR³—[(CH₂)₂O]$_{m5}$—(CH₂)₂— and A₃ represents —[(CH₂)₂O]$_{n4}$—(CH₂)₂—NR⁴—C(O)—(CH₂)$_{n5}$—, then A₆ represents a sequence —(CH₂)$_{m4}$—C(O)O—, -A₂-NH— or -A₂-NH—[(CH₂)₂O]$_{n4}$—(CH₂)₂—NR⁴—, with m4, R³, m5, n4, n5 and R⁴ as defined for the monomers of formula (I), and Z₁ is a hydrogen atom or a protective or activating group for amines or acids as a function respectively of the amine or carboxyl end functional group of the spacer arm A₆ to which Z₁ is bonded.

The monomers of formula (IIa) as defined above in which A₆ represents a sequence -A₂-NH— or -A₂-NH—[(CH₂)₂O]$_{n4}$—(CH₂)₂—NR⁴— and Z₁ represents an activating group for the amine functional group, forming, with the amine functional group to which it is bonded, a phosphoramidate monoester, a phosphoramidate diester, an H-phosphoramidate or a phosphoramidite, constitute a particular aspect of the invention. These monomers can be used in the supported synthesis of oligonucleotides, as described, for example, in patent application WO 03/068787.

As for the monomers of formula (Ia), preference is given to the monomers of formula (IIa) as defined above in which at least one of the sequences A₂ and A₃ comprises a unit —[(CH₂)₂O]—$_m$ with m which represents m3, m5, n2 or n4 as defined for the monomers of (I).

Particular preference is given to the monomers of formula (IIha) as defined above in which:

A₂ represents —(CH₂)$_{m1}$—, with m1 as defined for the monomers of formula (I) and in particular m1=1, A₃ represents —[(CH₂)₂O]$_{n4}$—(CH₂)₂—NR⁴—C(O)—(CH₂)$_{n5}$—, with n4, n5 and R⁴ as defined for the monomers of formula (I) and in particular n4=2, n5=1 and R⁴=H, and A₆ represents —(CH₂)$_{m1}$—NH— or, preferably, —(CH₂)$_{m1}$—NH—[(CH₂)₂O]$_{n4}$—(CH₂)₂—NR⁴—, with m1, n4, R⁴ and n5 as defined for the monomers (I) and in particular m1=1, n4=2, n5=1 and R⁴=H, Z₁ is a hydrogen atom or a protective group for amines, for example chosen from the trifluoroacetyl, tert-butoxycarbonyl and 9-fluorenylmethoxycarbonyl groups, or else Z₁ represents an activating group for the amine functional group forming, with the amine functional group to which it is bonded, a phosphoramidate monoester, a phosphoramidate diester, an H-phosphoramidate or a phosphoramidite. The monomers (IIc) correspond to the following formula (IIc):

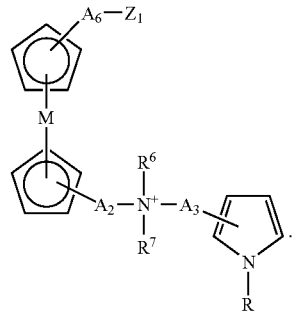

in which:

M, R, R⁶ and R⁷ are as defined for the monomers of formula (I),

A₂ represents —(CH₂)$_{m1}$—, —(CH₂)$_{m2}$—O—[(CH₂)₂O]$_{m3}$—(CH₂)₂— or —(CH₂)$_{m4}$—C(O)—NR³—[(CH₂)₂O]$_{m5}$—(CH₂)₂— with m1 to m5 and R³ as defined for the monomers of formula (I), $A_3$ represents $-(CH_2)_{n1}-$, $-[(CH_2)_2O]_{n2}-(CH_2)_{n3}-$ or $-[(CH_2)_2O]_{n4}-(CH_2)_2-NR^4-C(O)-(CH_2)_{n5}-$, with n1 to n5 and $R^4$ as defined for the monomers of formula (I), $A_6$ represents a spacer arm defined as follows:
when $A_2$ represents $-(CH_2)_{m1}-$ or $-(CH_2)_{m2}-O-[(CH_2)_2O]_{m3}-(CH_2)_2-$ and $A_3$ represents $-(CH_2)_{n1}-$ or $-[(CH_2)_2O]_{n2}-(CH_2)_{n3}-$, then $A_6$ represents a sequence -$A_2$-NH—, with m1, m2, m3, n1, n2 and n3 as defined for the monomers of formula (I), when $A_2$ represents $-(CH_2)_{m4}-C(O)-NR^3-[(CH_2)_2O]_{m5}-(CH_2)_2-$ and $A_3$ represents $-(CH_2)_{n1}-$ or $-[(CH_2)_2O]_{n2}-(CH_2)_{n3}-$, then $A_6$ represents a sequence $-(CH_2)_{m4}-C(O)O-$ or -$A_2$-NH—, with m4, $R^3$, m5, n1, n2 and n3 as defined for the monomers of formula (I), when $A_2$ represents $-(CH_2)_{m1}-$ or $-(CH_2)_{m2}-O-[(CH_2)_2O]_{m3}-(CH_2)_2-$ and $A_3$ represents $-[(CH_2)_2O]_{n4}-(CH_2)_2-NR^4-C(O)-(CH_2)_{n5}-$, then $A_6$ represents a sequence -$A_2$-NH— or -$A_2$-NH—$[(CH_2)_2O]_{n4}-(CH_2)_2-NR^4-$, with m1, m2, m3, n4, $R^4$ and n5 as defined for the monomers of formula (I), when $A_2$ represents $-(CH_2)_{m4}-C(O)-NR^3-[(CH_2)_2O]_{m5}-(CH_2)_2-$ and $A_3$ represents $-[(CH_2)_2O]_{n4}-(CH_2)_2-NR^4-C(O)-(CH_2)_{n5}-$, then $A_6$ represents a sequence $-(CH_2)_{m4}-C(O)O-$, -$A_2$-NH— or -$A_2$-NH—$[(CH_2)_2O]_{n4}-(CH_2)_2-NR^4-$, with m4, $R^3$, m5, n4, n5 and $R^4$ as defined for the monomers of formula (I), and $Z_1$ is a hydrogen atom or a protective or activating group for amines or acids as a function respectively of the amine or carboxyl end functional group of the spacer arm $A_6$ to which $Z_1$ is bonded.

The monomers of formula (IIc) as defined above in which $A_6$ represents a sequence -$A_2$-NH— or -$A_2$-NH—$[(CH_2)_2O]_{n4}-(CH_2)_2-NR^4-$ and $Z_1$ represents an activating group for the amine functional group, forming, with the amine functional group to which it is bonded, a phosphoramidate monoester, a phosphoramidate diester, an H-phosphoramidate or a phosphoramidite, constitute a particular aspect of the invention. These monomers can be used in the supported synthesis of oligonucleotides, as described, for example, in patent application WO 03/068787.

As for the monomers of formula (Ic), preference is given to the monomers of formula (IIc) as defined above in which at least one of the sequences $A_2$ and $A_3$ comprises a unit $-[(CH_2)_2O]_m-$ with m which represents m3, m5, n2 or n4 as defined for the monomers (I).

Particular preference is given to the monomers of formula (IIc) as defined above in which:
$A_2$ represents $-(CH_2)_{m1}-$, with m1 as defined for the monomers of formula (I) and in particular m1=1,
$A_3$ represents $-[(CH_2)_2O]_{n4}-(CH_2)_2-NR^4-C(O)-(CH_2)_{n5}-$, with n4, n5 and $R^4$ as defined for the monomers of formula (I) and in particular n4=2, n5=1 and $R^4$=H, and
$A_6$ represents $-(CH_2)_{m1}-NH-$ or, preferably, $-(CH_2)_{m1}-NH-[(CH_2)_2O]_{n4}-(CH_2)_2-NR^4-$, with m1, n4, $R^4$ and n5 as defined for the monomers (I) and in particular m1=1, n4=2, n5=1 and $R^4$=H, $Z_1$ is a hydrogen atom or a protective group for amines, for example chosen from the trifluoroacetyl, tert-butoxycarbonyl and 9-fluorenylmethoxycarbonyl groups, or else $Z_1$ represents an activating group for the amine functional group forming, with the amine functional group to which it is bonded, a phosphoramidate monoester, a phosphoramidate diester, an H-phosphoramidate or a phosphoramidite.

The monomers (IIb) correspond to the following formula (IIb):

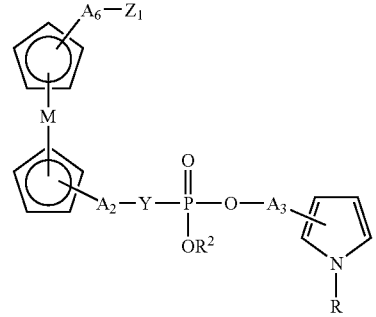

(IIb)

in which:
M, R, $A_2$, Y, $R^2$ and $A_3$ are as defined for the monomers (I),
$A_6$ represents a spacer arm defined as follows:
when $A_2$ represents $-(CH_2)_{m1}-$ or $-(CH_2)_{m2}-O-[(CH_2)_2O]_{m3}-(CH_2)_2-$ and $A_3$ represents $-(CH_2)_{n1}-$ or $-[(CH_2)_2O]_{n2}-(CH_2)_{n3}-$, then $A_6$ represents a sequence -$A_2$-Y—, with m1, m2, m3, n1, n2 and Y as defined for the monomers (I), when $A_2$ represents $-(CH_2)_{m4}-C(O)-NR^3-[(CH_2)_2O]_{m5}-(CH_2)_2-$ and $A_3$ represents $-(CH_2)_{n1}-$ or $-[(CH_2)_2O]_{n2}-(CH_2)_{n3}-$, then $A_6$ represents a sequence $-(CH_2)_{m4}-C(O)O-$ or -$A_2$-Y—, with m4, $R^3$, m5, n1, n2, n3 and Y as defined for the monomers (I), when $A_2$ represents $-(CH_2)_{m1}-$ or $-(CH_2)_{m2}-O-[(CH_2)_2O]_{m3}-(CH_2)_2-$ and $A_3$ represents $-[(CH_2)_2O]_{n4}-(CH_2)_2-NR^4-C(O)-(CH_2)_{n5}-$, then $A_6$ represents a sequence -$A_2$-Y— or -$A_2$-Y—P(O)(OR$^2$)—O—$[(CH_2)_2O]_{n4}-(CH_2)_2-NR^4-$, with m1, m2, m3, n4, $R^4$, n5, Y and $R^2$ as defined for the monomers (I), when $A_2$ represents $-(CH_2)_{m4}-C(O)-NR^3-[(CH_2)_2O]_{m5}-(CH_2)_2-$ and $A_3$ represents $-[(CH_2)_2O]_{n4}-(CH_2)_2-NR^4-C(O)-(CH_2)_{n5}-$, then $A_6$ represents a sequence $-(CH_2)_{m4}-C(O)O-$, -$A_2$-Y— or -$A_2$-Y—P(O)(OR$^2$)—O—$[(CH_2)_2O]_{n4}-(CH_2)_2-NR^4-$, with m4, $R^3$, m5, n4, n5, $R^2$, $R^4$ and Y as defined for the monomers (I), $Z_1$ represents a hydrogen atom or a protective or activating group for alcohols, amines or carboxylic acids as a function respectively of the amine, alkoxy or carboxyl end functional group of the spacer arm $A_6$ to which $Z_1$ is bonded.

The monomers of formula (IIb) as defined above in which $A_6$ represents -$A_2$-Y— or -$A_2$-Y—P(O)(OR$^2$)—O—$[(CH_2)_2O]_{n4}-(CH_2)_2-NR^4-$ and $Z_1$ represents an activating group for the amine or alkoxy functional group of the spacer arm $A_6$ to which $Z_1$ is bonded, respectively forming, with the amine functional group to which it is bonded, a phosphoramidate monoester, a phosphoramidate diester, an H-phosphoramidate or a phosphoramidite or, with the alkoxy functional group to which it is bonded, a phosphodiester, a phosphotriester, an H-phosphonate or a phosphoramidite, constitute a particular aspect of the invention and can be used in the supported synthesis of oligonucleotides.

Advantageously, as for the monomers of formula (Ib), the monomers (IIb) exhibit one or more of the following catalysts:
Y=O;
$R^2$ represents a hydrogen atom;
$A_2$ and $A_3$ respectively represent $-(CH_2)_{m1}-$ and $-(CH_2)_{n1}-$ and $A_6$ represents the sequence $-(CH_2)_{m1}-O-$ with m1 and n1 as defined for the monomers (I) and in particular m1=3 and n1=2.

Likewise, among the monomers of formula (III), the monomers of formulae (IIIa), (IIIc) and (IIIb) as defined below are preferred. These monomers are formulae (III), (IIIa), (IIIc) and (IIIb) correspond to the monomers of formulae (II), (IIa), (IIc) and (IIb) on which a biological ligand has been covalently coupled, optionally via a spacer arm, to the reactive functional group (F) present on the ionizable free arm substituting the metallocene. The monomers (IIIa) correspond to the formula (IIIa):

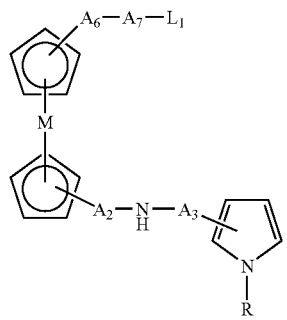
(IIIa)

in which $A_7$ represents a connecting arm or a direct bond, $L_1$ represents a biological ligand and $A_2$, $A_3$, $A_6$ and R are as defined for the compounds of formula (IIa), for which the preferred values indicated during the definition of the compounds of formula (IIa) also apply.

The monomers (IIIc) correspond to the formula (IIIc):

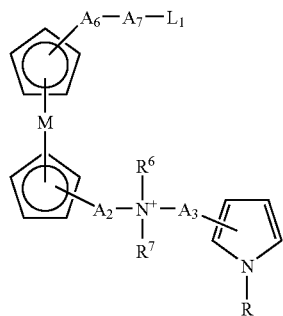

in which $A_7$ represents a connecting arm or a direct bond, $L_1$ represents a biological ligand and $A_2$, $A_3$, $A_6$, $R^6$, $R^7$, and R are as defined for the compounds of formula (IIc), for which the preferred values indicated during the definition of the compounds of formula (IIc) also apply.

The monomers (IIIb) correspond to the formula (IIIb):

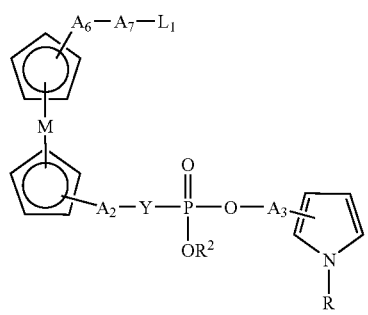
(IIIb)

in which $A_7$ represents a connecting arm or a direct bond, $L_1$ represents a biological ligand and $A_2$, $A_3$, $A_6$, R and $R^2$ are as defined for the compounds (IIb), for which the preferred values indicated during the definition of the compounds of formula (IIb) also apply.

Advantageously, the monomers (I), (Ia), (Ib), (Ic), (II), (IIa), (IIb), (IIc), (III), (IIIa), (IIIb) and (IIIC) exhibit one or more of the following characteristics:

the bonding between the ionizable connecting arm and the pyrrole unit takes place at the 3 position of the pyrrole, M is iron, R is a hydrogen atom.

These various monomers can be prepared as described below, in the case of the ferrocenes, by these synthetic routes can be applied to the other metallocenes. In that which will follow, R, $R^1$ to $R^7$, Y, n, n1 to n5, m1 to m5, p1, p2, q1 and q2 are as defined for the monomers (I).

The preparation of the monomers of formula (I), (Ia) (Ic) or (Ib) in which $A_1$ is a sequence $-A_2-X-A_3-$ with X which represents $—NR^1—$, $—Y—P(O)(OR^2)—O—$ or $—N^+(R^6R^7)—$ will first of all be explained in detail.

First of all, the preparation can be carried out by analogy with the methods described for the monomers (Ia.1), (Ic.1) and (Ib.1) given in the examples. For the other monomers, the following methods can be employed:

1) when $A_2$ represents $—(CH_2)_{m2}—O—[(CH_2)_2O]_{m3}—(CH_2)_2—$, it is possible:

1a) either, when X represents $—O—P(O(OR^2)—O—$, to form the monomer of following formula (I):

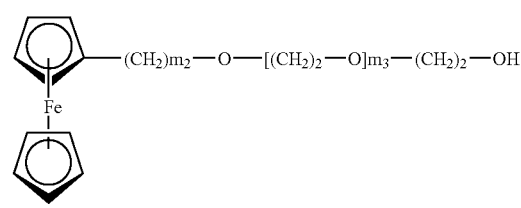
(1)

as described in Chem. Eur. J., 1996, 2, 877 or J. Organometallic Chemistry, 2001, 630, 266. This monomer (1) will then be reacted with the corresponding pyrrole substituted by a chain $A_3$ carrying an end hydroxyl functional group, one of the hydroxyl functional groups, preferably that situated on the side of the ferrocene, having been activated beforehand in the form of a phosphoramidite.

1b) or, when X represents $—NR^1—$, $—N^+(R^6R^7)—$ or $—NH—P(O)(OR^2)—O—$, to directly form a poly(alkoxy)amine arm by condensation of an alkoxide (3) with a ferrocene substituted by a $—(CH_2)_{m2}—OH$ group (4) (prepared according to Nucleic Acids Research, 2004, 32, 5310-5319), in the following way (SCHEME 1), to form the monomer (2):

SCHEME 1

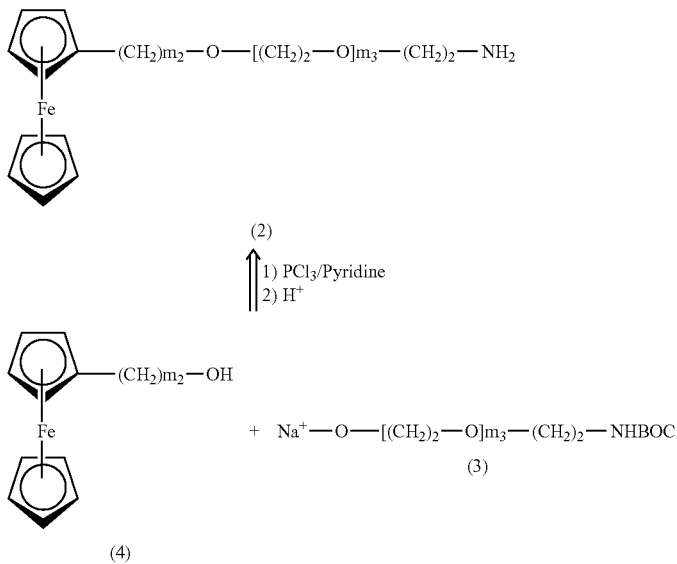

The ferrocene (2) thus obtained can then be coupled, when X represents —NR$^1$—, with the corresponding pyrrole substituted by a chain carrying an end halogen atom, said chain being chosen in order to obtain the desired arm $A_3$, or else, when X represents —NH—P(O)(OR$^2$)—O—, the end amine functional group of the ferrocene (2) will be activated in the form of a phosphoramidite in order to be able to be coupled to a pyrrole carrying an end hydroxyl on the arm $A_3$.

2) when $A_2$ represents —(CH$_2$)$_{m4}$—C(O)—NR$^3$—[(CH$_2$)$_2$O]$_{m5}$—(CH$_2$)$_2$—, it is possible to form a ferrocene (5) substituted by an arm —(CH$_2$)$_{m4}$—C(O)—NR$^3$—[(CH$_2$)$_2$O]$_{m5}$—(CH$_2$)$_2$—NH$_2$ (or OH) by condensation of a ferrocene (6) substituted by an arm —(CH$_2$)$_{m4}$—C(O)OH (prepared according to WO 01/81446) with an amine (7) in the presence of EDC (1-ethyl-3-[3-(dimethylamino)propyl]carbodiimide) and of N-hydroxysuccinimide, as described in the following SCHEME 2:

SCHEME 2

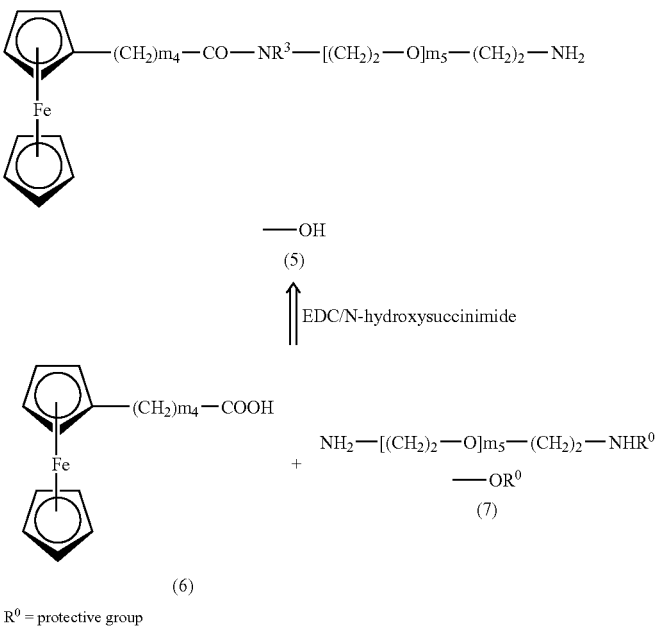

$R^0$ = protective group

3) The substituted pyrroles involved can, for their part, be prepared as follows:

3a) when $A_3$ represents $-(CH_2)_{n1}-$ or $-[(CH_2)_2O]_{n2}-(CH_2)_{n3}-$, the pyrrole substituted by a $-(CH_2)_{n1}-Br$ or $-(CH_2)_{n3}-[O(CH_2)_2]_{n2}-Br$ group can be obtained from the pyrrole substituted by a $-(CH_2)_{n1}-OH$ group (prepared according to Synth. Commun., 1996, 26, 1289) or a $-(CH_2)_{n3}-[O(CH_2)_2]_{n2}-OH$ group (prepared according to FR 2849038) respectively, for example in the presence of $CBr_4$ and of triphenylphosphine in methanol at 0° C.

3b) when $A_3$ represents $-[(CH_2)_2O]_{n4}-(CH_2)_2-NR^4-C(O)-(CH_2)_{n5}-$, the pyrrole substituted by a $-(CH_2)_{n5}-C(O)-NR^4-(CH_2)_2-[O(CH_2)_2]_{n4}-$ group can be obtained from the pyrrole (8) substituted by a $-(CH_2)_{n5}-C(O)-NR^4-(CH_2)_2-[O(CH_2)_2]_{n4}-$ OH group. This pyrrole (8) is obtained as follows, by condensation of a pyrrole (9) carrying an activated ester functional group (prepared according to Synthetic Metals, 1999, 100, 89) and of an amine (10) as illustrated in SCHEME 3:

SCHEME 3

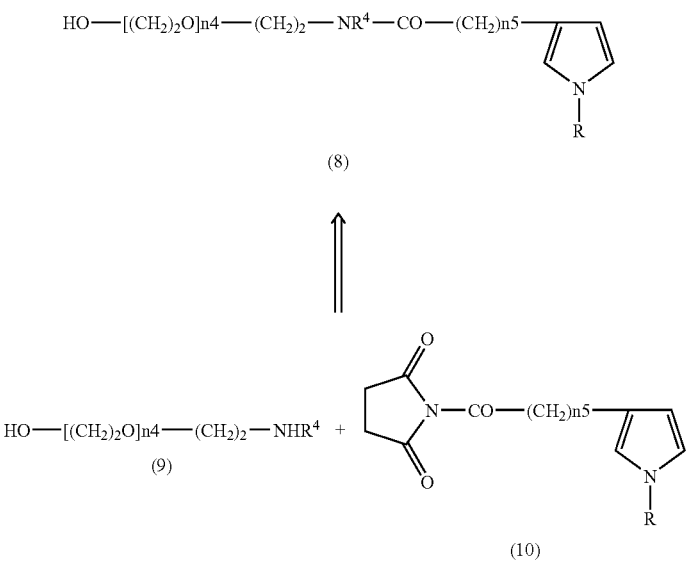

4) When $A_2=-(CH_2)_{m1}-$, $A_3=-(CH_2)_{n1}-$, with $m_1+n_1$ between 2 and 6, and $X=-NR^1-$, the monomers will be obtained from a halogenated ferrocene (11) and an aminated pyrrole (12) (for example prepared according to WO 01/81446) below:

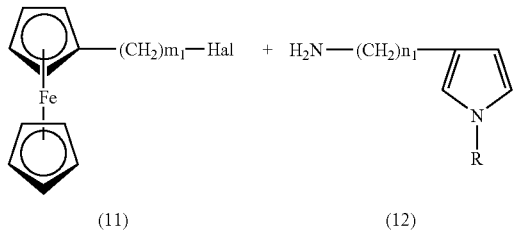

The preparation of the monomers (I) in which $A_1$ represents $-A_4-[NH(CH_2)_2]_n-A_5-$ can, for its part, be carried out as explained in detail below:

1) when $A_4=-(CH_2)_{p1}-$ and $A_5=-(CH_2)_{q1}-$, the preparation will be carried out by condensation of a halogenated ferrocene (13) with a pyrrole (14) substituted by a polyamine. This pyrrole substituted by a polyamine will be obtained conventionally by coupling of a polyamine (15) to a haloalkylated pyrrole (16), as illustrated in SCHEME 4.

SCHEME 4

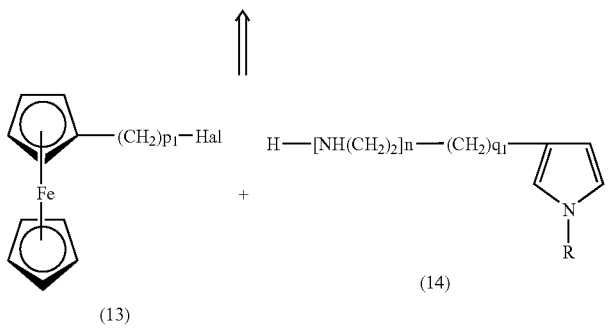

(13)    (14)

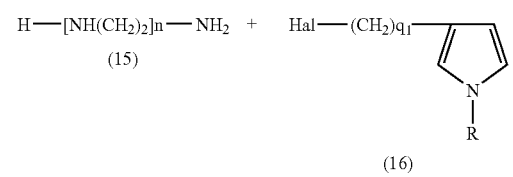

(15)    (16)

The halogenated ferrocene (13) can be synthesized according to the protocol described in J. Electroanal. Chem., 1994, 370, 203. The haloalkylated pyrrole, in the case where Hal=Br, can be prepared as described above.

2) When $A_4=$—$(CH_2)_{p2}$—CO—, the preparation can be carried out by coupling a ferrocene (17) (prepared according to WO 01/81446) carrying an activated ester functional group to a pyrrole (18) carrying a polyamine arm, as represented in SCHEME 5.

SCHEME 5

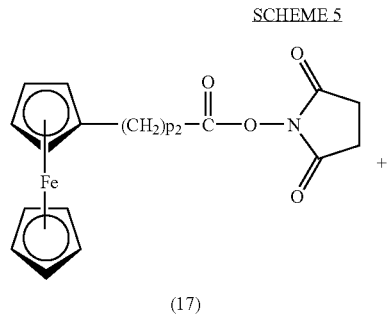

(17)

-continued

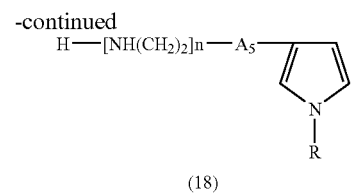

(18)

The pyrrole (16) can be prepared as in SCHEME 4 if $A_5$ represents —$(CH_2)_{q1}$—.

When $A_5=$—$NR^5$—C(O)—$(CH_2)_{q2}$—, the pyrrole (19) (SCHEME 6) can be formed and will be coupled either to the ferrocene (13) or to the ferrocene (17) described above. The pyrrole (19) can be prepared from a polyamine (20) and a pyrrole carrying an activated ester functional group (21).

SCHEME 6

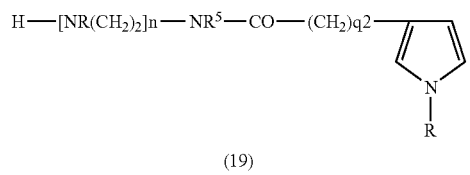

(19)

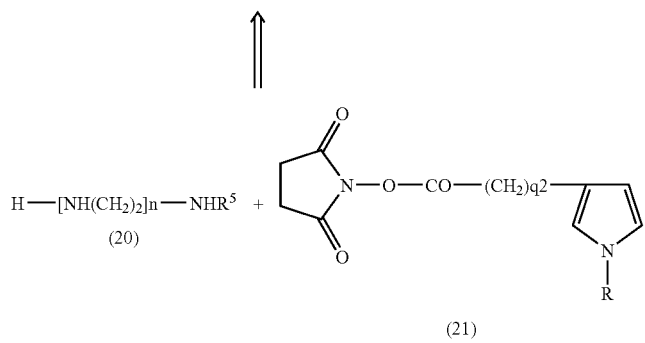

The monomers (II), (IIa), (IIc) and (IIb) exhibit a metallocene group with a 1-1'-disubstitution. The substitutions of the metallocene exhibit a degree of symmetry which is encountered in $A_1$ and $A_6$.

The reactions explained in detail above for functionalizing the metallocenes will thus be carried out so as to obtain two functionalizations, if required, or a single functionalization, depending on the structure desired for $A_6$. For this, a selective reaction or a protection/deprotection well known to a person skilled in the art can be employed.

Furthermore, for the preparation of monosubstituted or disubstituted metallocene, a person skilled in the art will be in a position to adapt the methods of synthesis described, in particular in WO 03/068787 or in Chem. Rev., 2004, 104, 5931-5985.

The examples given later illustrate such reactions.

It will also be possible to employ, as other synthetic routes, when $A_6$=—$(CH_2)_{n4}$—C(O)—O—, a bis(activated ester) ferrocene of formula (22):

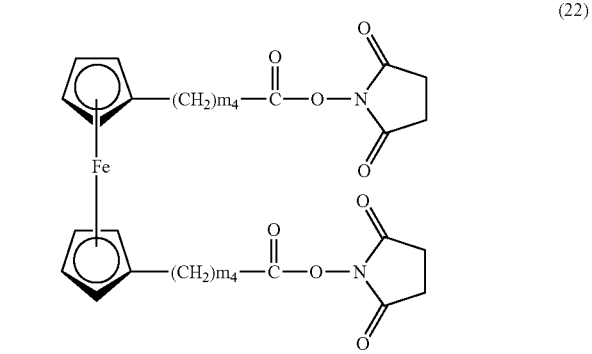

prepared according to patent application WO 01/81446. This compound can then be coupled, according to techniques well known to a person skilled in the art, to one equivalent of an aminated pyrrole with a structure chosen in order to obtain the desired sequence $A_3$.

Likewise, when $A_6$=—$(CH_2)_{m1}$—O— and $A_2$=—$(CH_2)_{m1}$—O—$P(O)OR^2$—, it will be possible to use a ferrocene (23) carrying two hydroxyl functional groups, one of these functional groups being protected with a (tert-butyl)dimethylsilyl chloride, (TBDMSiCl), for example, to result in the protected ferrocene (24). This protected ferrocene can then be coupled to a phosphoramidite chloride (25) to result in the protected ferrocene (26), which can subsequently, after deprotection, be coupled to a pyrrole-3-alkanol to result in the ferrocene (27). The free hydroxyl functional group of the ferrocene (27) can then be coupled to another phosphoramidite chloride to result in the compound (28).

This preparation is illustrated in SCHEME 7, in the case where $A_6$=—$(CH_2)_3$—O—;

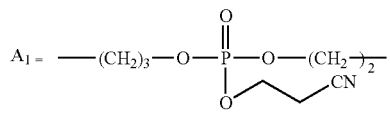

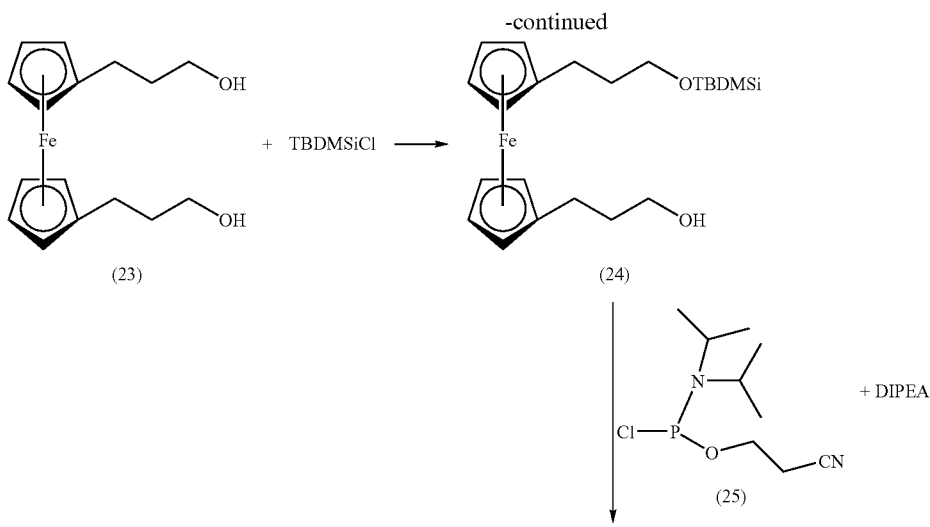
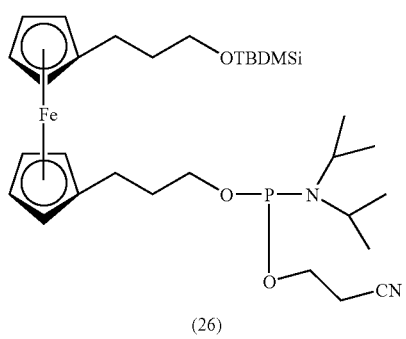
1) Pyrrole-3-ethanol 1.1 eq./
   0.45M tetrazole in acetonitrile
2) Butanone peroxide (0.67%/CH$_2$Cl$_2$)
3) TBAF/THF
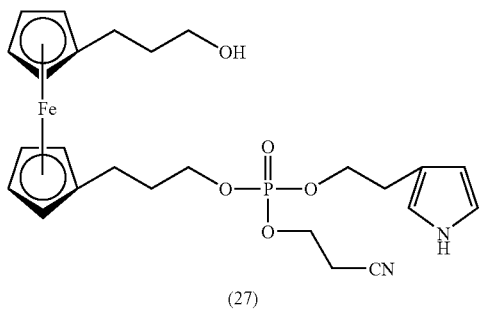
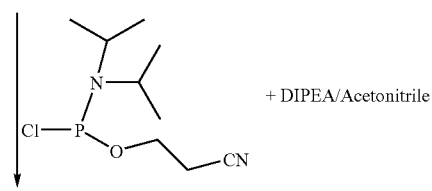

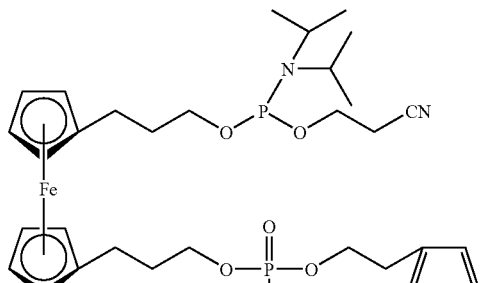

(28)

The monomers (III) (IIIa), (IIIc) and (IIIb), for their part, are obtained by coupling a ligand to the corresponding monomer (II), (IIa), (IIc) or (IIb) carrying a reactive functional group $F_1$ ($Z_1$=H) of the amine, hydroxyl or carboxylic acid type. Generally, this coupling will be carried out via a spacer arm $A_7$, for example of polymer of alkyl chain type. The spacer arms which can be used to distance the biological ligand from the polymer chain obtained in the end are well known to a person skilled in the art. Any spacer arm which does not detrimentally affect the solubility or the electroactive properties of the monomer can be used. Mention may be made, by way of example, of the functional derivatives of jeffamines or maleic anhydride. This spacer arm is coupled to the reactive functional group $F_1$ and then the ligand is coupled to another reactive functional group $F_2$, for example of the activated ester type, carried by the spacer arm. The polymer arm can be a bifunctional polymer (polyethylene glycol bis(activated ester), for example) or a polyfunctional polymer (MAMVE: maleic anhydride-co-methyl vinyl ether, NVPNAS: N-vinylpyrrolidone-co-N-acryloyloxysuccinimide, NAMNAS: N-acryloylmorpholin-co-N-acryloyloxysuccinimide).

In the case where the monomer (II) is used for the supported synthesis of oligonucleotides, that is to say in the cases defined above where $Z_1$ represents an activating group for the amine or alkoxy functional group of the spacer arm $A_6$ to which $Z_1$ is bonded, respectively forming, with the amine functional group to which it is bonded, a phosphoramidate monoester, a phosphoramidate diester, an H-phosphoramidate or a phosphoramidite or, with the alkoxy functional group to which it is bonded, a phosphodiester a phosphotriester, an H-phosphonate or a phosphoramidite, then the spacer arm $A_7$ will be of the

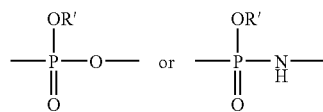

type, it being possible for the end of the arm $A_6$ bonded to the phosphorus atom to be an oxygen atom or a nitrogen atom, —NH— or —NR$^4$—.

As said above, the use of the monomers according to the invention makes possible targeting of the biomolecules on a spot of an electrode. Furthermore, this targeting can be carried out in a single stage.

Consequently, another object of the invention is to provide electroactive probes and electrodes at least partially covered with such a probe which are simpler to prepare and which make possible a more direct measurement of the probe ligand/target ligand interaction.

The term "electroactive probe" is understood to mean a probe, the electrochemical response of which is modified when a target ligand interacts in specific fashion with the probe ligands carried by the probe. Thus, the electrochemical signal is observed to be modified following the specific interaction with the analyte.

The term "target ligand" is understood to mean any molecule capable of interacting specifically with a probe ligand attached to the monomer according to the invention and thus capable of being detected with a copolymer or polymer according to the invention obtained from such a monomer. This target ligand can, for example, be a biomolecule, such as, for example, a nucleotide, in particular an oligonucleotide, a protein, an antibody, antigen, a peptide, a lipid, a steroid, a sugar or a nucleic acid. The probe ligand carried by the polymer is specific to the target ligand to be detected.

Another subject matter of the present invention is thus electroactive probes capable of being obtained by electropolymerization of at least two soluble monomers in accordance with the invention each carrying a biological ligand forming a conductive homopolymer. In particular, at least two monomers of formula (III), (IIIa), (IIIb) or (IIIc) as defined above will be used.

Even if they are not preferred, the electroactive probes in the form of a conductive homopolymer capable of being obtained by electropolymerization of at least two soluble monomers in accordance with the invention each carrying an amine, hydroxyl or carboxylic acid reactive functional group (F), optionally in the protected form, followed by coupling of said reactive functional group (F) to a biological ligand, form an integral part of the invention. In particular, a monomer of formula (II), (IIa), (IIb) or (IIc) as defined above will be used.

Preferably, a subject matter of the present invention is electroactive probes in the form of a conductive copolymer capable of being obtained by copolymerization between two different monomers, at least one of which is in accordance with the invention, at least one, and preferably just one, of the monomers carrying a biological ligand.

In particular, the copolymerization will be carried out starting from a monomer of formula (III), (IIIa), (IIIb) or (IIIc) and from a monomer (I), (Ia), (Ib) or (Ic) as defined above. A spacing of the probe biological ligands is thus obtained which makes it possible to improve the sensitivity. Use will advantageously be made of a pair of monomers (III)/(I) or (IIIa)/(Ia) or (IIIb)/(Ib) or (IIIc)/(Ic) in which M, $A_1$ and R are identical.

Here again, even if they are not preferred, the electroactive probes in the form of a conductive copolymer capable of being obtained by electropolymerization of at least one, and preferably just one, soluble monomer in accordance with the invention carrying an amine, hydroxyl or carboxylic acid reactive functional group (F), optionally in the protected form, followed by coupling of said reactive functional group (F) to a biological ligand, form an integral part of the invention. In particular, the copolymerization will be carried out starting from a monomer of formula (II), (IIa), (IIb) or (IIc) and from a monomer (I), (Ia), (Ib) or (Ic) as defined above. Advantageously, use will be made of a pair of monomers (II)/(I) or (IIa)/(Ia) or (IIb)/(Ib) or (IIc)/(Ic) in which M, $A_1$ and R are identical.

Another subject matter of the present invention is an electropolymerization process carried out in aqueous solution employing at least one of the monomers in accordance with the invention and in particular at least one of the monomers carrying a biological ligand.

This electropolymerization can be a homopolymerization.

In particular, a homopolymerization with a monomer of formula (III), (IIIa) or (IIIb) or (IIIc) as defined above will be carried out. A homopolymerization starting from at least two soluble monomers in accordance with the invention each carrying an amine, hydroxyl or carboxylic acid reactive functional group (F), optionally in the protected form, can also be carried out. This homopolymerization can then be followed by coupling of said reactive functional group (F) to a biological ligand. In particular, a monomer of formula (II), (IIa), (IIb) or (IIc) as defined above will be used.

Preferably, the electropolymerization will be a copolymerization carried out between two different monomers, at least one of which is in accordance with the invention. Preferably, at least one, and preferably just one, of the monomers carries a biological ligand. In particular, the copolymerization will be carried out starting from a monomer of formula (III), (IIIa), (IIIb) or (IIIc) and from a monomer (I), (Ia), (Ib) or (Ic) as defined above. Advantageously, use will be made of a pair of monomers (III)/(I) or (IIIa)/(Ia) or (IIIb)/(Ib) or (IIIc)/(Ic) in which M, $A_1$ and R are identical.

It is also possible to carry out a copolymerization of at least two different soluble monomers in accordance with the invention each carrying an amine, hydroxyl or carboxylic acid reactive functional group (F), optionally in the protected form. This copolymerization reaction in the aqueous phase will advantageously be followed by a coupling of said reactive functional group (F) to a biological ligand. In particular, the copolymerization will be carried out starting from a monomer of formula (II), (IIa), (IIb) or (IIc) and from a monomer (I), (Ia), (Ib) or (Ic) as defined above. Advantageously, use will be made of a pair of monomers (II)/(I) or (IIa)/(Ia) or (IIb)/(Ib) or (IIc)/(Ic) in which M, $A_1$ and R are identical.

Another subject matter of the present invention is the polymers capable of being obtained by such polymerization reactions, optionally followed by coupling with a biological ligand.

According to another of its aspects, another subject matter of the present invention is electrodes comprising a conductive support, all or part of the surface of which is coated with an electroactive probe as defined above.

Another subject matter of the present invention is a method for the detection of a target ligand in a biological sample, in which the sample is brought into contact with an electroactive probe as defined above carrying a probe ligand, under conditions appropriate for the probe ligand/target ligand interaction, and the difference in potential or in current emitted by the probe before and after being brought into contact with the sample is demonstrated and optionally quantified.

The polymers obtained from the monomers according to the invention can be used in particular in all applications in which biological ligands are targeted and immobilized on a solid support.

More particularly, these polymers can be obtained in the form of self-supporting films or in the form of a film on an electrode. This is because the electrode makes it possible, by measuring the current delivered during the reaction, to control the progress of the polymerization reaction. The electrode also makes it possible to measure the subsequent electrochemical responses of the polymer. The present invention thus also relates to an electrode comprising a conductive support coated at the surface with at least one electroactive conductive polymer functionalized with biological ligands according to the invention, that is to say an electroactive probe according to the invention.

Conductive supports for electrodes are known from the state of the art; mention will in particular be made of substrates made of metal or of carbon derivatives. For the manufacture of an electrode according to the invention, the polymer is generally deposited on the conductive support. The electrochemical polymerization is advantageously carried out at the surface of the electrode in order to obtain an electrode comprising a conductive support coated at the surface with a polymer according to the invention. In an advantageous embodiment of the invention, the electrode is obtained by depositing a layer of polymer at the surface of a support made of gold or of platinum.

Given that it is possible to limit and control electrochemical polymerization reactions at an electrode, the monomers according to the present invention make possible the immobilization and the targeting of biological ligands on small surfaces. This targeted electrocopolymerization makes it possible to produce a matrix of miniaturized and orderly points, each of the points carrying a defined biological ligand. In an advantageous embodiment, the invention thus also relates to a matrix of electrodes.

The invention thus also relates to a matrix of electrodes comprising at least one electrode according to the invention. Such matrices of electrodes can be provided in the form of a test card or analytical chip comprising a series of wells, each well corresponding to an electrode.

In an advantageous embodiment, the various electrodes of the matrix carry different biological ligands. According to a specific embodiment, the invention relates to a plurality of electrodes or of microelectrodes attached to a solid support; these electrodes are coated with a copolymer according to the invention and advantageously carry different biological ligands. Such matrices of electrodes can advantageously be obtained by targeted electropolymerization of monomers according to the invention and in particular by copolymerization of at least two monomers, at least one of which carries a biological ligand, such as a monomer of formula (III), (IIIa), (IIIb) or (IIIc), and at least one not functionalized with a ligand, such as a monomer of formula (I), (Ia), (Ib) or (Ic).

The electrodes and the matrices of electrodes according to the invention can be used in particular for the detection of analyses capable of being present in a sample and capable of reacting specifically with the biological ligands carried by the polymer.

The present invention makes it possible to detect a target ligand in any type of sample. In a specific embodiment of the invention, the sample is a biological sample. Advantageously, this sample may have been taken from a patient for diagnostic purposes. The sample can, for example, be urine, blood, serum, plasmid, cell extracts or a body fluid. As the probe is electroactive, its electrochemical response will be modified when a target ligand specifically interacts with the probe ligand carried by the polymer. The electroactive conductive polymer according to the invention thus translates the interaction with the target ligand into an electrochemical signal. The specific interaction of a target ligand with the oligonucleotides carried by the polymer produces a modification in the electrochemical response of the polymer studied with respect to that obtained before introduction of the target ligand. Advantageously, the detection of the target ligand is thus carried out by an electrical measurement. The term "electrical measurement" is understood to mean the measurement of a variation of potentiometric type, such as the variation in the oxidation potential of the polymer, or the measurement of a variation of amperometric type, by variation in the oxidation current observed at a given potential. These variations are measured in a rapid, sensitive and quantitative fashion according to methods well known to a person skilled in the art.

In an advantageous embodiment of the invention, the electrical measurement consists of the measurement of a variation in potential or of a variation in current. In a specific embodiment of the invention, cyclic voltammetry is used. This is an electroanalytical method which consists in scanning a potential range in one direction and then in the other, at a constant rate. The voltammogram obtained gives the current response of the electrochemical system studied and allows it to be characterized.

Detection methods by an electrical measurement are preferred with the polymers according to the invention. However, other conventional detection methods known to a person skilled in the art can also be used.

In a particularly advantageous embodiment of the invention, the specific interaction between the target ligand and the probe ligand carried by the polymer can be detected with the electrode which has been used for the electropolymerization of the polymer. For example, the hybridization of a nucleic acid complementary to oligonucleotides carried by the polymer can be detected by electrical measurement on the electrode which supports the polymer according to the invention.

The hybridization of oligonucleotides can be monitored directly by measuring the variation in the electrochemical signal detected or else via an enzymatic reaction. In this case, the target oligonucleotide for example carries a biotin. After introduction of streptavidin-peroxidase and of the substrate for the enzyme, detection can be carried out either at the level of the substrate or at the level of the electrochemical signal.

In the same way, it is possible to monitor, by virtue of the variations in the electrochemical signal, protein/protein interactions of the antibody/antigen and antibody/protein type in particular.

It is also possible to use the polymers capable of being obtained with the monomers according to the invention for the assaying of phosphate ions, in the context of the monitoring of a PCR, for example; to study the activity of an enzyme; in applications in molecular electronics, as described, for example, in Science, 2004, 306, 2048-2074.

The examples of the preparation of monomers and the electrochemical characterization of the polymers obtained which will follow are given by way of illustration.

A. Examples of the Preparation of Monomers

I—Monomer (Ia.1)

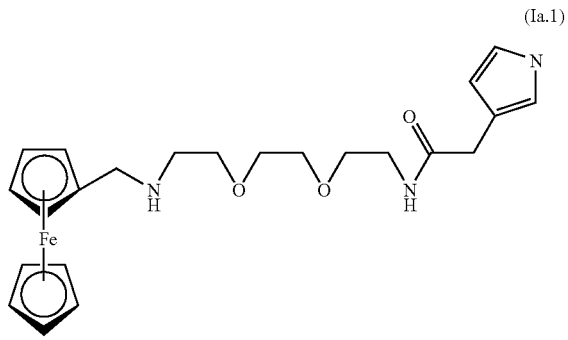

The monomer Ia.1 is repaired according to the following scheme:

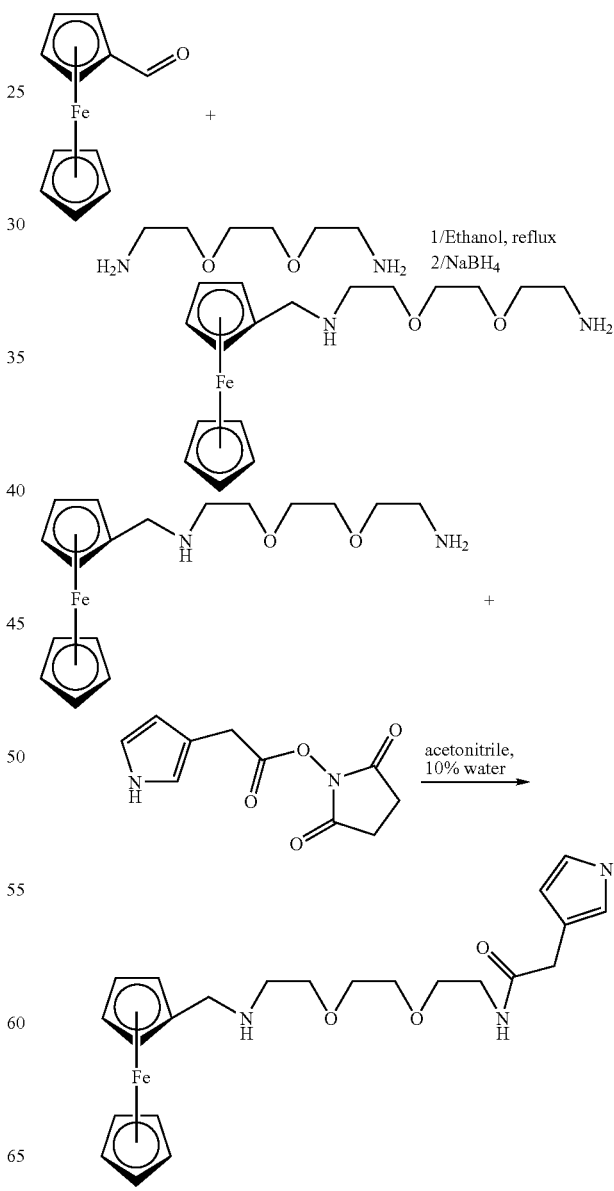

I-1 Synthesis of (10-amino-5,8-dioxa-2-azadecyl)ferrocene 158 mg (1.06 mmol, 1.10 eq.) of 1,8-diamino-3,6-dioxaoctane (Aldrich) are introduced into 5 ml of absolute ethanol in a twin-necked round-bottomed flask equipped with a reflux condenser. 207 mg (0.97 mmol, 1 eq.) of ferrocene carboxaldehyde (ABCR), dissolved in 15 ml of absolute ethanol, are added thereto dropwise using a pressure-equalizing dropping funnel. Once the addition is complete, the reaction medium is brought to reflux of the ethanol (80° C.). After continual stirring at this temperature for 6 hours, the reaction medium is cooled to ambient temperature and left overnight with stirring. In order to reduce the imine formed to give an amine, 40 mg (1.06 mmol, 1.10 eq.) of sodium borohydride (Aldrich) are added directly to the reaction medium. Reaction is allowed to take place at ambient temperature with stirring for 2 hours. The ethanol is subsequently evaporated and the medium is taken up in dichloromethane and then purified on a silica column with a dichloromethane/methanol/triethylamine 80-18-2 mixture.

90 mg of product are obtained in the form of a yellow solid (0.26 mmol, 26%).

$^1$H NMR (200 MHz, CDCl$_3$, TMS): δ 2.95 ppm (t, 2H, CH$_2$CH$_2$NH), 3.10 ppm (t, 2H, CH$_2$CH$_2$NH$_2$), 3.72 ppm (m, 8H, NCH$_2$CH$_2$O, OCH$_2$CH$_2$O), 3.91 ppm (s, 2H, FcCH$_2$NH), 4.20 ppm (s, 7H, Cp H), 4.40 ppm (s, 2H, Cp H).

I-2 Pyrrole Activated ester/(10-amino-5,8-dioxa-2-azadecyl)ferrocene Coupling 89 mg of (10-amino-5,8-dioxa-2-azadecyl)ferrocene (0.26 mmol, 1 eq.) are introduced into a round-bottomed flask and dissolved in 1 ml of a 90/10 acetonitrile/water mixture. 0.26 mmol (1 eq.) of pyrrole phthalimidyl or succinimidyl activated ester obtained in section 1.2.b, dissolved beforehand in 1 ml of solvent, is slowly added. The mixture is left stirring at ambient temperature for 30 minutes (phthalimidyl ester) to 4 hours (succinimidyl ester). The reaction medium is subsequently purified on a silica column with a dichloromethane/methanol 90/10 mixture.

15 mg of a yellow solid are obtained (0.03 mmol, 13%), which solid is soluble in water up to a concentration of at least 30 mM.

$^1$H NMR (200 MHz, CD$_3$OD, TMS): δ 3.03 ppm (t, 2H, CH$_2$CH$_2$NHCH$_2$), 3.34 ppm (m, 2H, CH$_2$CH$_2$NHC(O), CH$_2$Py), 3.50 ppm (t, 2H, OCH$_2$CH$_2$NHC(O)), 3.60 ppm (s, 4H, OCH$_2$CH$_2$O), 3.63 ppm (t, 4H, CH$_2$NCH$_2$CH$_2$O), 3.99 ppm (s, 2H, FcCH$_2$NH), 4.20 ppm (s, 5H, Cp H), 4.27 ppm (t, 2H, Cp H), 4.39 ppm (t, 2H, Cp H), 6.01 ppm (s, 1H, CH=CH—N), 6.67 ppm (m, 2H, CH—CH)

MS electrospray: M+H$^+$=454, M+Na$^+$=475, fragmentation=199

II Monomer (Ic.1)

The monomer (Ic.1) is obtained from the monomer (Ia.1) by methylation reaction.

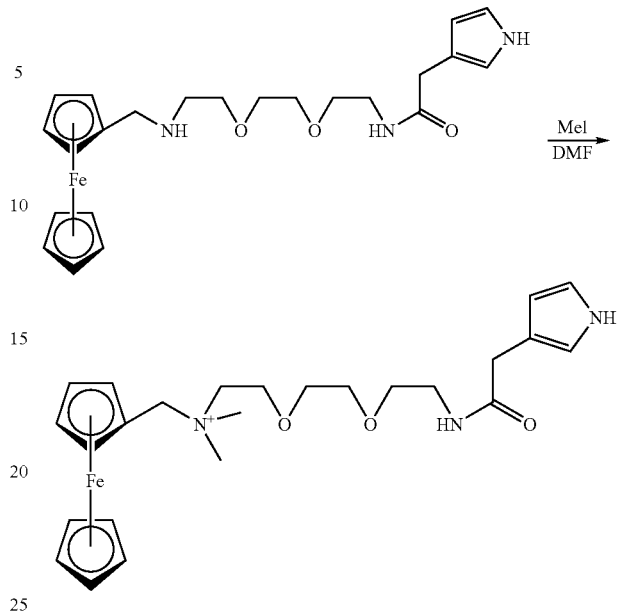

1 eq. of the monomer Ia.1 is dissolved in DMF (Dimethylformamide) at a concentration of 0.15M in a single-necked round-bottomed flask. 200 eq. of iodomethane are then carefully added. A reflux condenser system is installed in order to prevent evaporation of the iodomethane. Reaction is allowed to take place at ambient temperature with stirring for 12 h and then 200 eq. of iodomethane are again added. Reaction is allowed to take place at 24 h. The excess iodomethane is subsequently evaporated and purification is carried out on a normal phase silica column. The desired product (which is the least polar) is collected in the form of an orange-yellow oil. The yield is 60%. The product is subsequently passed through an anion-exchange column to exchange the iodide counterions against chlorides.

This molecule has a solubility in pure water at 25° C. of greater than 50 mM.

$^1$H NMR (200 MHz, CD$_3$OD, TMS): δ 2.97 ppm (s, 6H, CH$_3$), 3.34 ppm (m, CH$_2$CH$_2$NHC(O)), 3.39 ppm (s, CH$_2$Py), 3.43 ppm (t, 2H, CH$_2$CH$_2$N$^+$(CH$_3$)$_2$CH$_2$), 3.50 ppm (t, 2H, OCH$_2$CH$_2$NHC(O)), 3.60 ppm (s, 4H, OCH$_2$CH$_2$), 3.63 ppm (t, 4H, CH$_2$NCH$_2$CH$_2$O), 3.99 ppm (s, 2H, FcCH$_2$NH), 4.20 ppm (s, 5H, Cp H), 4.27 ppm (s, 2H, Cp H), 4.39 ppm (s, 2H, Cp H), 6.01 ppm (s, 1H, CH=CH—N), 6.67 ppm (d, 2H, CH—CH)

MS electrospray: M+H$^+$=482

III—Monomer (Ib.1)

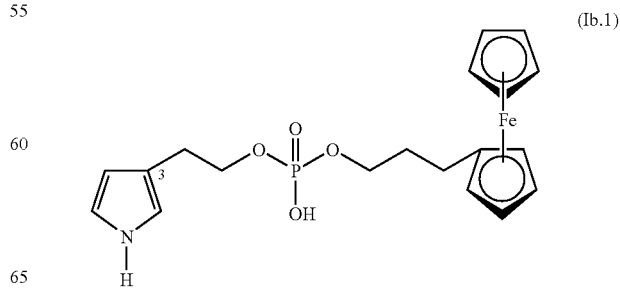

(Ib.1)

Step 1: Synthesis of 1-[3-O-(2-cyanoethyl-N,N-di-isopropylphosphor-amidityl)propyl]ferrocene

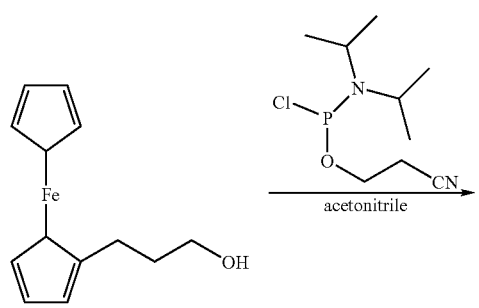

MW = 244.12
C₁₃H₁₆FeO

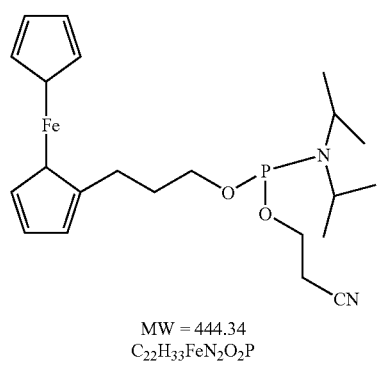

MW = 444.34
C₂₂H₃₃FeN₂O₂P

Ferrocene monopropanol (53.3 mg, 0.218 mmol) is coevaporated three times in 1 ml of anhydrous acetonitrile. After having taken up the orange oil in 1 ml of anhydrous acetonitrile under argon, DIPEA (120 μL, 0.480 mmol), and then chlorophosphine (42 μL, 0.240 mmol) are added. The progress of the reaction is monitored by TLC (cyclohexane-ethyl acetate-triethylamine (49.5/49.5/1)) on plates premigrated in the same eluent: after reacting for 10 min, starting material is no longer present; the reaction medium is concentrated by half.

The crude reaction product obtained is purified on silica gel neutralized with a cyclohexane-triethylamine (99:1) mixture; eluent ethyl acetate-cyclohexane (50:50).

The fractions comprising the product are combined and concentrated. The oil is coevaporated three times with an ethanol/acetonitrile mixture in order to remove the triethylamine.

The oil is taken up in 1 ml of acetonitrile and then filtered through a 0.45 μm PVDF filter; the product is concentrated.

Weight of product obtained: 0.116 g

Stage 2: Synthesis of 3-ferrocenylpropyl 2-cyanoethyl 2-(3-pyrrolyl)ethyl phosphate triester

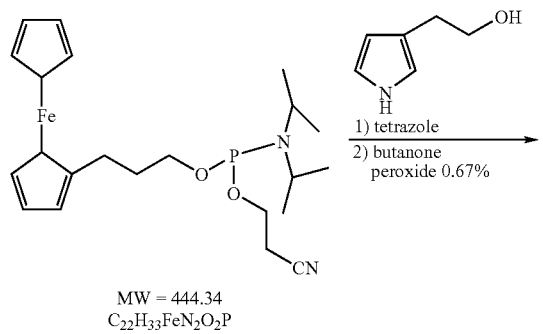

MW = 444.34
C₂₂H₃₃FeN₂O₂P

-continued

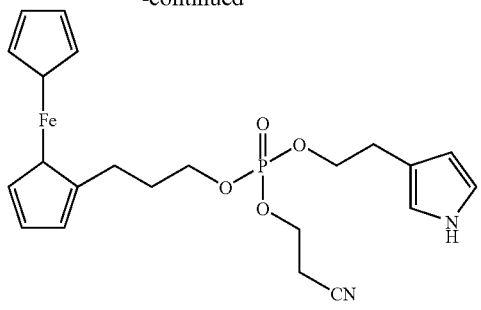

MW = 470.29
C₂₂H₂₇FeN₂O₄P

Pyrrole-3-ethanol (26 mg, 0.233 mmol) is coevaporated twice in 1 ml of anhydrous acetonitrile and then taken up in 1 ml of anhydrous acetonitrile.

The 0.45M solution of tetrazole in acetonitrile (1 ml, 0.436 mmol) is added in the presence of a few pellets of molecular sieve (3 angstroms). The ferrocene phosphoramidite derivative obtained in stage 1 (97 mg, 218 mmol) is added in solution in anhydrous acetonitrile (1 ml). The solution becomes orange. The reaction is monitored by TLC in the cyclohexane-ethyl acetate-triethylamine (49.5/49.5/1) eluent. After reacting for 1 hour, no more starting material remains and the oxidation solution (butanone peroxide 0.67% in dichloromethane) (2 ml) is added. The solution becomes brown.

After reacting for 30 min, 20 ml of dichloromethane are added and the solution becomes cloudy as the tetrazole is insoluble. The solution is filtered and then extracted three times with a saturated NaHCO₃ solution and then once with a saturated NaCl solution.

The organic phase is dried over Na₂SO₄, filtered and concentrated.

Weight of crude product obtained: 0.155 g

The product is purified on silica gel neutrallized beforehand with a dichloomethane-triethylamine (99:1) mixture; eluent: dichloromethane-methanol (90:10).

53.3 mg of the expected product are obtained in the form of an orange-yellow oil; this corresponds to a yield of 52%; however, 65 mg of impure product are also obtained.

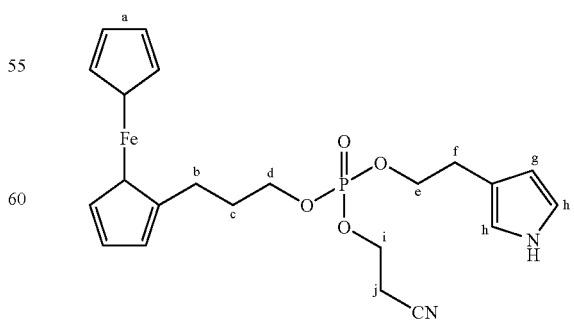

¹H NMR (CDCl₃) 200 MHz:

1.8 (m, 2H, Hc), 2.424 (m, 2H, Hb), 2.597-2.678 (m, 4H, Hj and CH$_2$ TEA), 2.908 (m, 2H, Hf), 3.842 (q, 2H, Hd), 4.147-4.010 (m, 18H, Ha, Hd, He), 6.0120 (b, 1H, Hg), 6.670 (b, 2H, Hh)

Stage 3: Synthesis of 3-ferrocenylpropyl 2-(3-pyrrolyl)ethyl phosphate diester (Ib.1)

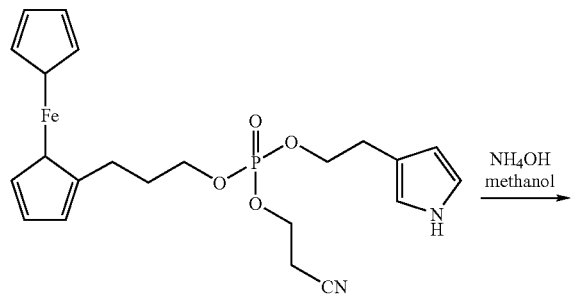

MW = 470.29
C$_{22}$H$_{27}$FeN$_2$O$_4$P

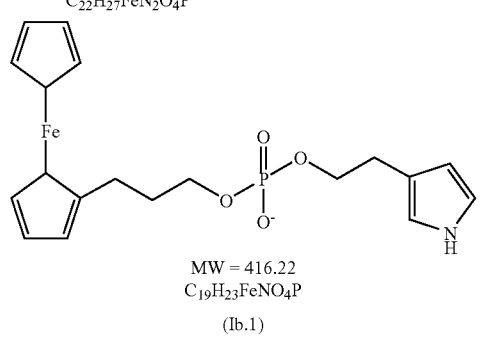

MW = 416.22
C$_{19}$H$_{23}$FeNO$_4$P (Ib.1)

2 ml of concentrated aqueous ammonia are added to 50 mg of 3-ferrocenylpropyl 2-cyanoethyl 2-(3-pyrrolyl)ethyl phosphate triester (obtained in stage 2) in solution of 1 ml of methanol in a Wheaton tube. A precipitate is formed and is dissolved by addition of 1 ml of methanol. The reaction is monitored by TLC, dichloromethane-methanol (85:15), visualization by UV (254 nm) and by vanillin. After 3 hours at ambient temperature, there is little change. The tube is placed in an oven at 60° C. for 2 hours; all the starting material has been consumed. 0.5 ml of TEA is added to the reaction medium before concentrating it, in order to prevent polymerization of the pyrrole. The crude reaction product thus obtained is purified on silica gel conditioned with a dichloromethane-triethylamine (99:1) mixture. An elution gradient is necessary for this purification: dichloromethane-methanol 100:0 to 85:15.

After purification, 21.1 mg (0.05 mmol, 48%) of an orange-yellow oil are obtained.

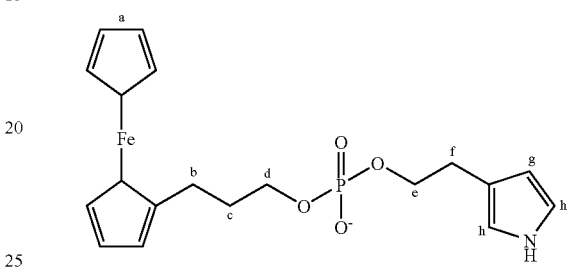

$^1$H NMR (CDCl$_3$) 200 MHz:
1.786-1.857 (m, 4H, Hc); 2.406 (t, 2H, Hb, J$^3_{bc}$=7.2 Hz); 2.858 (t, 2H, Hf, J$^3_{ef}$=6.4 Hz), 3.887 (m, 2H, He, J$^3_{ef}$=6.4 Hz), 3.962-4.075 (m, 15H, Ha, Hd, impurity); 6.110 (b, 1H, Hg), 6.678 (b, 2H, Hh).
$^{31}$P NMR (CDCl$_3$) 200 MHz:
Presence of a single phosphorus-comprising product at 0.7224 ppm
MS (ESI):
[M+H$^+$]=417.1, [M+Na$^+$]=439.9, [M+2Na$^+$]=461.8

IV-Monomer (IIa.1)

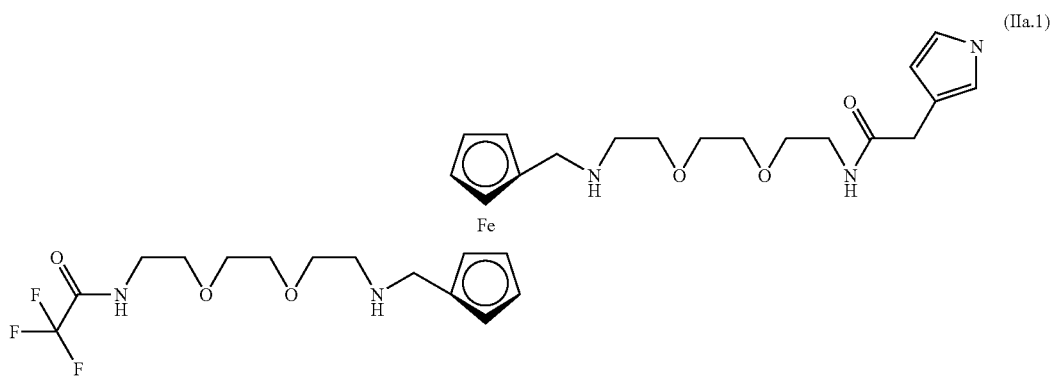

(IIa.1)

The monomer (IIa.1) is prepared according to the following scheme:

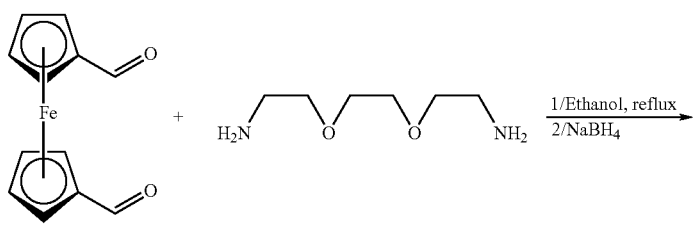

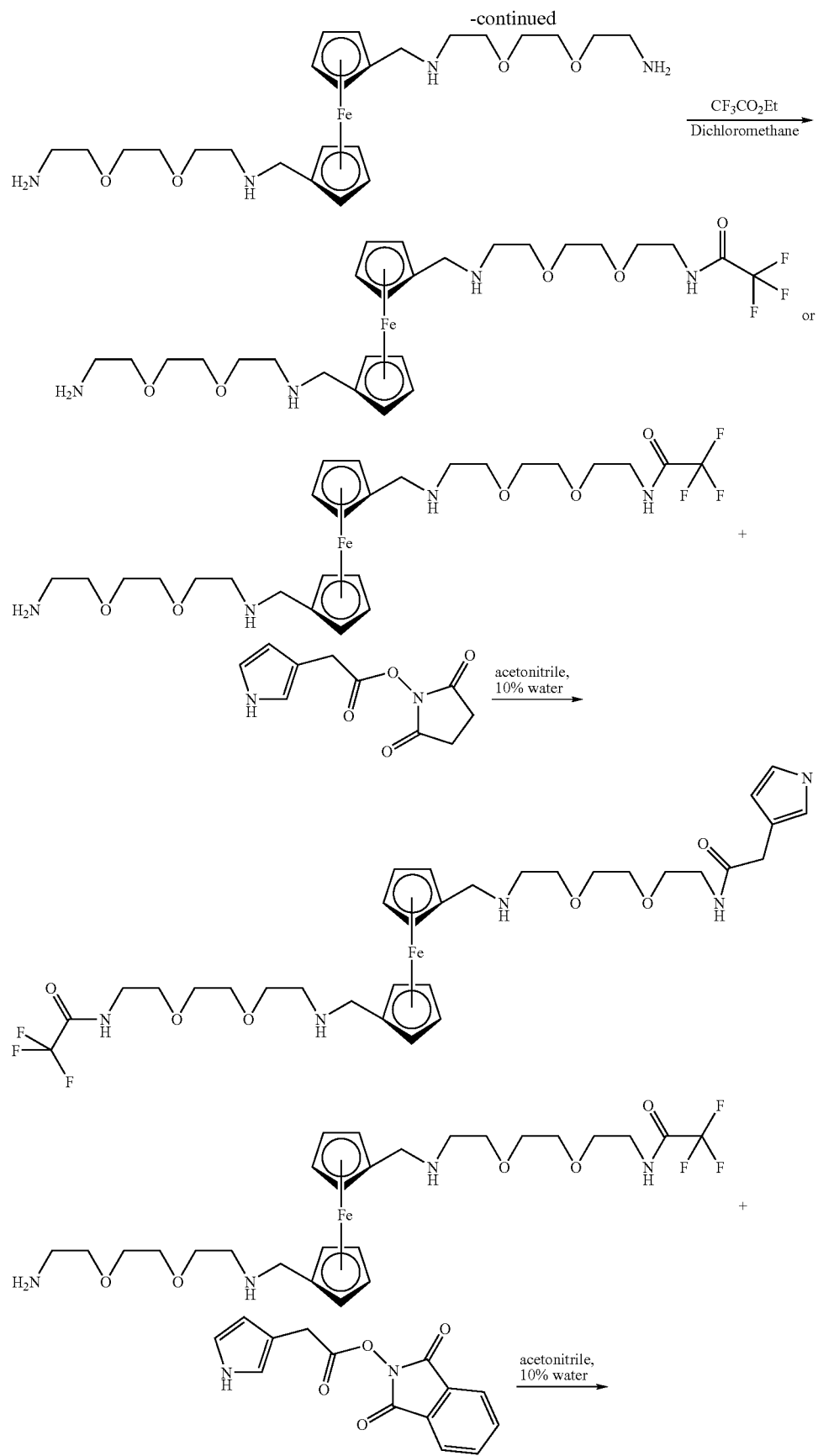

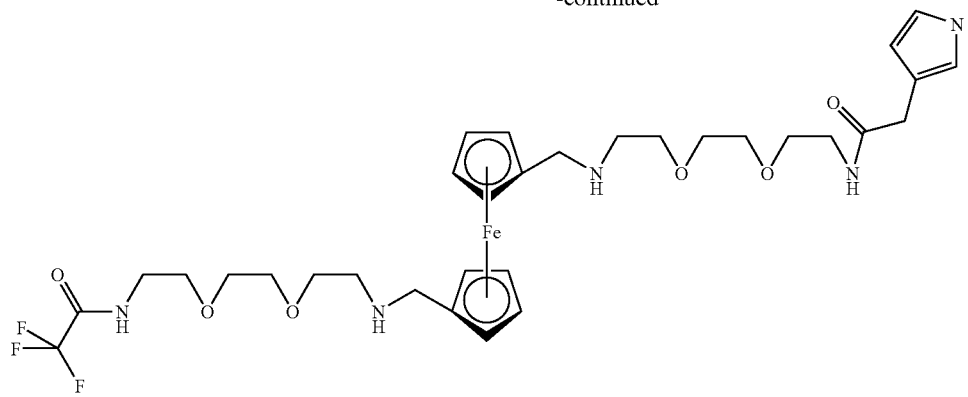

IV-1 Synthesis of bis(10-amino-5,8-dioxa-2-azadecyl)ferrocene 304 mg (2.05 mmol, 2.5 eq.) of 1,8-diamino-3,6-dioxaoctane (Acros Organics) are introduced into 5 ml of absolute ethanol in a twin-necked round-bottomed flask equipped with a reflux condenser. 200 mg (0.82 mmol, 1 eq.) of ferrocene dicarboxaldehyde (Aldrich), dissolved in 15 ml of absolute ethanol, are added thereto dropwise using a pressure-equalizing dropping funnel. Once the addition is complete, the reaction medium is brought to reflux of the ethanol (80° C.). After continual stirring at this temperature for 6 hours, the reaction medium is cooled to ambient temperature and left stirring overnight. In order to reduce the imine formed to give an amine, 186 mg (4.92 mmol, 6 eq.) of sodium borohydride (Aldrich) are added directly to the reaction medium. Reaction is allowed to take place at ambient temperature for 2 hours with stirring. The ethanol is subsequently evaporated and the medium is taken up in water and then purified on a reverse phase silica column with a 50/50 water-acetone mixture. 41 mg (0.08 mmol, 10%) of product are obtained in the form of a brown oil.

$^1$H NMR (500 MHz, CDCl$_3$, TMS): δ 1.92 ppm (s, 6H, CH$_2$CH$_2$NH, CH$_2$CH$_2$NH$_2$), 2.83 ppm (m, 8H, CH$_2$CH$_2$NH, CH$_2$CH$_2$NH$_2$), 3.49 ppm (m, 8H, NCH$_2$CH$_2$O), 3.60 ppm (m, 12H, FcCH$_2$NH, OCH$_2$CH$_2$O), 4.06 ppm (t, 4H, Cp H), 4.15 ppm (t, 4H, Cp H).

MS electrospray: M+H$^+$=507, M+Na$^+$=529, fragmentation=359

IV-2 Pyrrole Activated (Phthalimidyl or Succinimidyl) ester/bis(10-amino-5,8-dioxa-2-azadecyl)ferrocene Coupling

IV-2a Trifluoroacetyl Monoprotection 286 mg of bis(10-amino-5,8-dioxa-2-azadecyl)ferrocene (0.56 mmol, 1 eq.) are coevaporated on a rotary evaporator 3 times with anhydrous acetonitrile and once with anhydrous dichloromethane. The coevaporation is carried out under an inert atmosphere (argon). 3 ml of anhydrous dichloromethane are subsequently introduced into this round-bottomed flask and then 80 mg of ethyl trifluoroacetate (0.56 mmol, 1 eq.) are slowly added over 2 hours. After reacting for 6 hours, an additional 24 mg (0.17 mmol, 0.3 eq.) of ethyl trifluoroacetate are added. The reaction was allowed to run overnight. The medium is then concentrated and purified on a silica column with a dichloromethane/methanol/triethylamine 80/18/2 mixture. A brown oil is obtained with a yield of 50%.

MS electrospray: M+H$^+$=603, M+Na$^+$=625, fragmentation=454

IV-2b Synthesis of a Pyrrole Activated (Phthalimidyl or Succinimidyl) Ester The synthesis was carried out according to the protocol described in Korri-Youssoufi H. et al., J. Am. Chem. Soc., 1997, 119(31), 7388-7389 and according to the following schemes:

Pyrrole carrying an ester functional group activated by a succinimide group

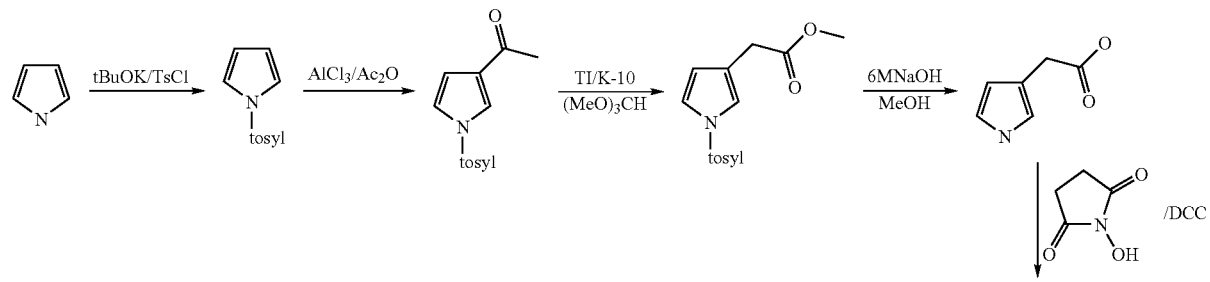

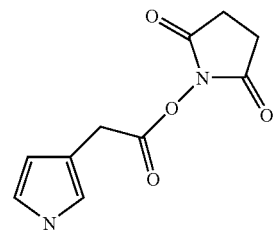

Pyrrole carrying an ester functional group activated by a phthalimide group

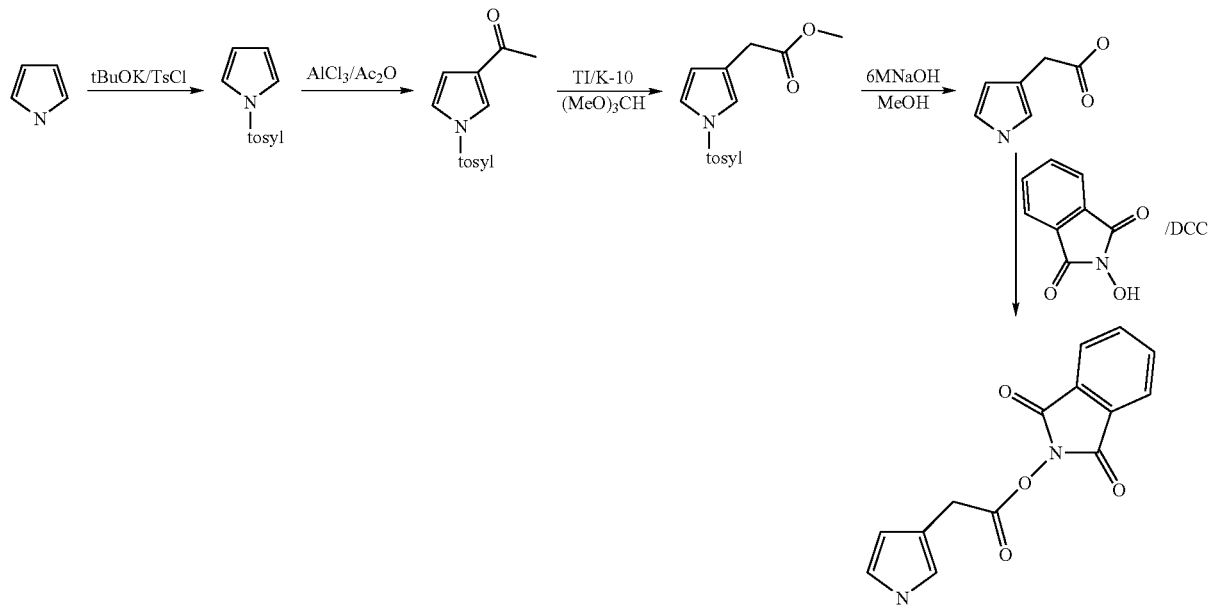

IV-2c Coupling with the Pyrrole Activated (Phthalimidyl ou Succinimidyl) Ester 88 mg of bis(10-amino-5,8-dioxa-2-azadecyl)ferrocene (0.15 mmol, 1 eq.) monoprotected with a trifluoroacetyl group obtained in section IV-2a are introduced into a round-bottomed flask and dissolved in 375 μL of a 90/10 acetonitrile/water mixture. 48 mg of pyrrole phthalimidyl ester or 40 mg of pyrrole succinimidyl ester (0.18 mmol, 1.2 eq.) obtained in section IV-2b, dissolved beforehand in 375 ml of solvent, are run in slowly. The mixture is left stirring at ambient temperature for 4 hours. The reaction medium is subsequently purified on a silica column with an 80/20 dichloromethane/methanol mixture. 18 mg (0.02 mmol, 17%) of a yellow-brown oil are obtained, which oil is soluble in water at least up to a concentration of 100 mM.

$^1$H NMR (500 MHz, d-DMSO, TMS): δ 2.81 ppm (q, 4H, CH$_2$CH$_2$NHCH$_2$), 3.36 ppm (t, 4H, C(O)NCH$_2$CH$_2$O), 3.42 ppm (t, 4H, OCH$_2$CH$_2$NC(O)), 3.53 ppm (m, 14H, CH$_2$Py, OCH$_2$CH$_2$O, CH$_2$NCH$_2$CH$_2$O); 3.63 ppm (d, 4H, FcCH$_2$NH), 4.16 ppm (s, 4H, Cp H), 4.24 ppm (s, 4H, Cp H), 5.92 ppm (s, 1H, CH=CH—N), 6.60 ppm (d, 2H, CH—CH), 7.42 ppm (s (broad), 1H, NH py)

$^{19}$F NMR (200 MHz, d-DMSO, TMS): δ-74.71 ppm (C(O)CF$_3$)

MS electrospray: M+H$^+$=710, M+Na$^+$=732, fragmentations=455, 466

V Monomer (IIa.2)

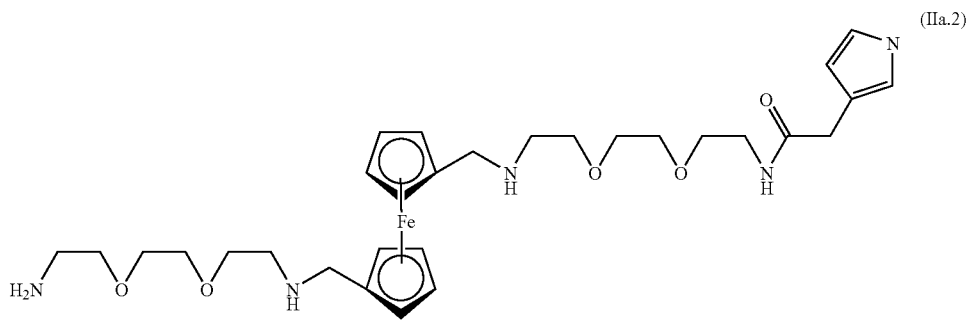

This monomer is obtained from the monomer (IIa.1). It is sufficient to carry out a deprotection of the primary amine (removal of the trifluoroacetyl group) as illustrated in the following scheme.

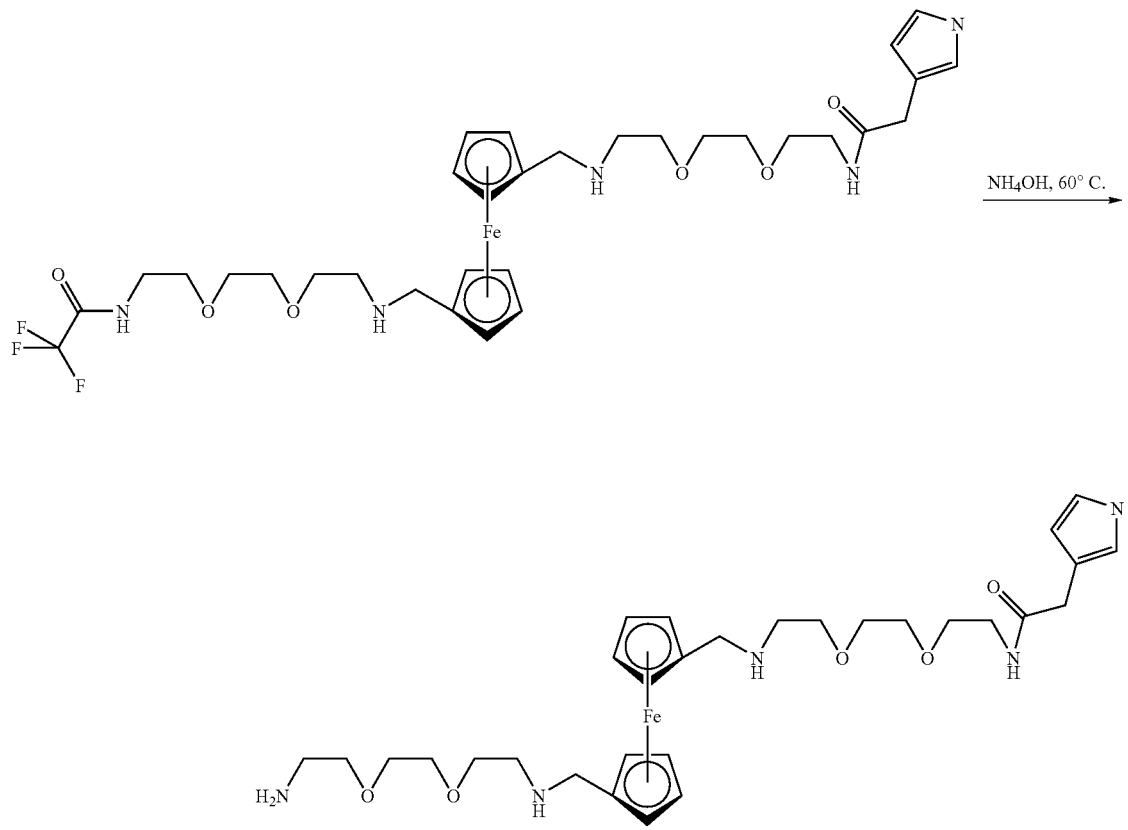

For this, 1 eq. of monomer (IIa.1) is introduced into a sealed 4 ml Wheaton tube. It is a third filled with a 28% ammonium hydroxide solution (Aldrich). It is closed and left in an oven at 60° C. overnight. The aqueous ammonia is subsequently evaporated on a rotary evaporator. Approximately 600 mg of product are obtained in the form of a brown oil which is soluble to more than 100 mM in water.

$^1$H NMR (200 MHz, d-DMSO, TMS): δ 2.73 ppm (m, CH$_2$CH$_2$NHCH$_2$, CH$_2$CH$_2$NH$_2$,) 2.93 ppm (t, C(O)NCH$_2$CH$_2$O), 3.09 ppm (t, 2H, OCH$_2$CH$_2$NC(O)), 3.35 ppm (s, 4H, OCH$_2$CH$_2$O), 3.53 ppm (t, ???, CH$_2$NCH$_2$CH$_2$O, NH$_2$CH$_2$CH$_2$O), 3.60 ppm (s, 2H, CH$_2$Py), 3.77 ppm (d, 4H, FcCH$_2$NH), 4.30 ppm (s, 4H, Cp H), 4.42 ppm (s, 4H, Cp H), 6.13 ppm (s, 1H, CH=CH—N), 6.82 ppm (d, 2H, CH—CH), 7.87 ppm (s (broad), 1H, NH py)

MS electrospray: M+H$^+$=614, M+Na$^+$=636, fragmentations=359, 455

VI—Monomer (IIb.1)

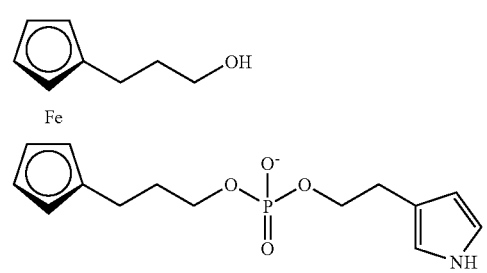

The monomer (IIb.1) is prepared according to the following scheme:

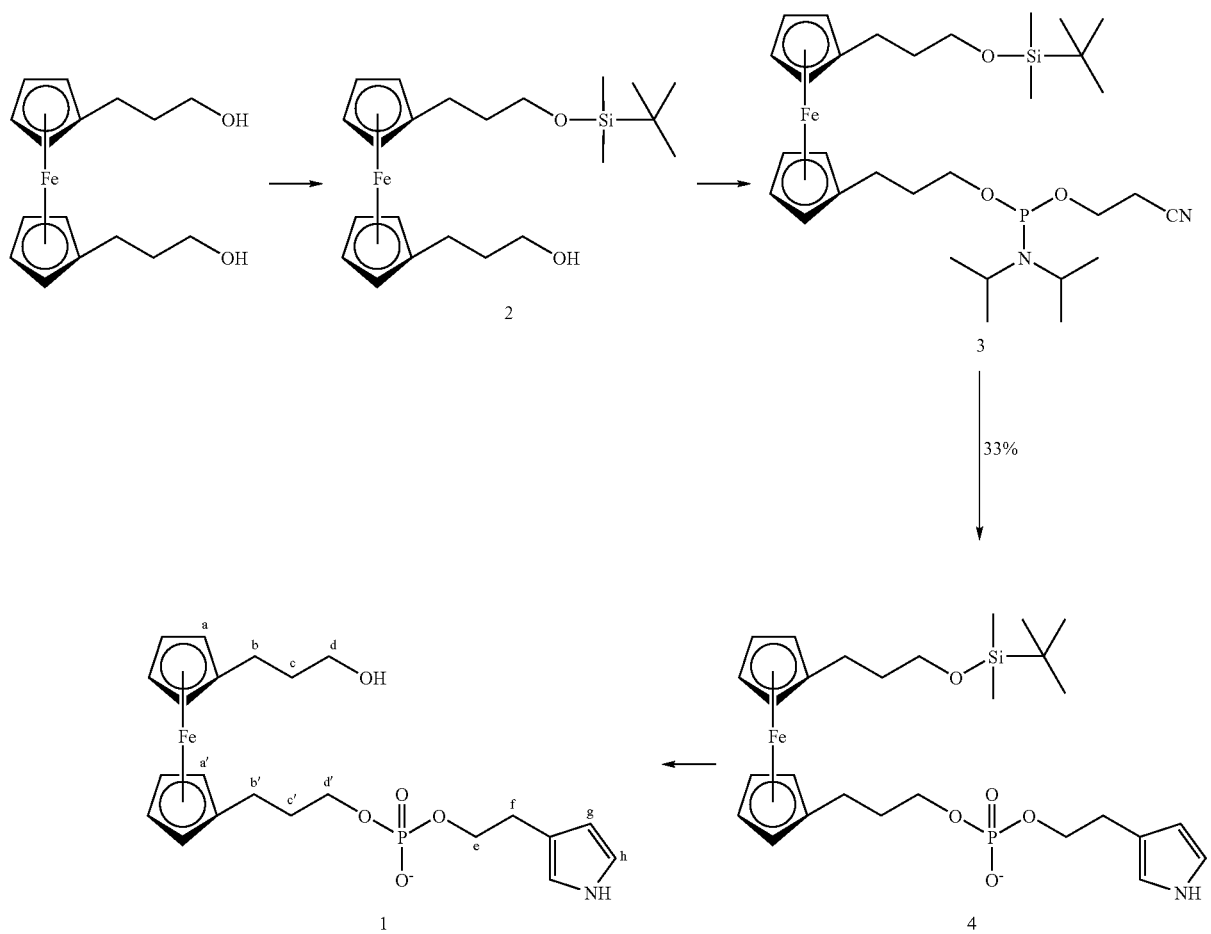

VI-1 Synthesis of 1-[3-O-tert-butyldimethylsilylpropyl]-1'-[3'-hydroxypropyl]-ferrocene (Intermediate 2 in the Above Figure)

1,1'-dihydroxypropylferrocene (Ezus, Lyons) (0.15 g, 0.496 mmol) was coevaporated three times in acetonitrile (3×2.5 ml) before dissolving in 5 ml of anhydrous acetonitrile. 0.05 g of imidazole (0.745 mmol), 45 μL of DIPEA (0.125 mmol) and 150 mg of tert-butyldimethylsilyl chloride (0.994 mmol) were then successively added to the reaction medium. The solution was stirred for 90 min. The reaction medium was then cooled to 0° C. before adding 2 ml of water to halt the reaction. The solvents were then evaporated to dryness under reduced pressure. The crude reaction product obtained was taken up in 40 ml of dichloromethane. The organic phase was washed twice with a saturated sodium bicarbonate solution (2×20 ml) and then dried over sodium sulfate. After evaporating the solvents under reduced pressure, the product was purified by chromatography on silica gel (prior neutralization of the silica with TEA) with a gradient of methanol in dichloromethane. After drying, an orange oil was obtained which corresponds to the pure product (0.102 g, 39% yield).

$^1$H NMR (200 MHz, CDCl$_3$) δ (in ppm): 0.06 (s, 6H, Si—(CH$_3$), 0.91 (s, 9H, CH$_3$ tBu), 1.68-1.83 (m, 4H, Hc, Hc'), 2.32-2.44 (m, 4H, Hb, Hb'), 3.59-3.68 (m, 4H, Hd, Hd'), 3.99 (s, 8H, Ha-Ha').

VI-2 Synthesis of 1-[3-O-tert-butyldimethylsilylpropyl]-1'-[3'-O-((2-cyano-ethyl)(N,N-diisopropyl) phosphoramidityl)propyl]ferrocene (Intermediate 3 in the Above Figure)

0.103 g of compound 2 (0.246 mmol) was coevaporated 3 times in anhydrous acetonitrile (3×3 ml) and then taken up in 3 ml of this same solvent. The solution was stirred and placed under an argon stream. DIPEA (94 μL, 0.545 mmol) and chlorophosphine (60 μl, 0.270 mmol) were then added to the reaction medium through a septum. After reacting for 30 minutes, the solution was concentrated under reduced pressure to a volume of 1 ml. The product was purified directly by chromatography or silica gel (prior neutralization of the silica with TEA) with a gradient of methanol in dichloromethane. After drying, an orange oil was obtained which corresponds to the pure product (0.121 g, 80% yield).

$^1$H NMR (200 MHz, CDCl$_3$) δ (in ppm): 0.06 (s, 6H, Si—(CH$_3$), 0.91 (s, 9H, CH$_3$ tBu), 1.19 (d, 12H, CH$_3$ iPr), 1.68-1.77 (m, 4H, Hc, Hc'), 2.32-2.36 (m, 4H, Hb, Hb'), 2.63 (t, 2H, CH$_2$—CN), 3.56-3.65 (m, 6H, Hd, Hd', CH$_2$—(CH$_2$—CN), 3.83-3.97 (m, 2H, CH— iPr), 3.98 (s, 8H, Ha-Ha'). NMR $^{31}$P (200 MHz, CDCl$_3$) δ: 147.92 ppm.

VI-3 Synthesis of {3-[1'-(3'-O-tert-butyldimethylsi-lylpropyl)ferrocen-1-yl]propyl}[2-(3-pyrrolyl)ethyl] phosphate diester (Intermediate 4 in the Above Figure)

0.024 g of 3-(hydroxyethyl)pyrrole (0.215 mmol) was coevaporated 3 times in anhydrous acetonitrile (3×3 ml) and then taken up in 3 ml of this same solvent, in the presence of argon. 1.1 ml of a 0.45M solution of tetrazole in acetonitrile (0.489 mmol) were then added to the solution, followed by 0.121 g of compound 3 (0.215 mmol). The reaction medium was then stirred for 30 minutes at ambient temperature under argon. The product was then oxidized by the addition to the reaction medium of a solution of butanone peroxide in dichloromethane (4.5 ml, 0.67%). After stirring for 45 minutes, 25 ml of dichloromethane were then added. The organic phase was washed twice with a saturated sodium bicarbonate solution (2×15 ml) and then dried over a sodium sulfate. After evaporating the solvents under reduced pressure, the crude residual product was dissolved in ammonia (30% aqueous) and then placed in a sealed flask at 60° C. for 16 hours. After evaporating the solvents under reduced pressure, the product was purified by chromatography on silica gel (prior neutralization of the silica with TEA) with a gradient of methanol in dichloromethane. After drying, an orange oil was obtained which corresponds to the pure product (0.042 g, 33% yield).

$^1$H NMR (200 MHz, CDCl$_3$) δ (in ppm): 0.06 (s, 6H, Si—(CH$_3$), 0.91 (s, 9H, CH$_3$ tBu), 1.33 (t, CH$_3$ TEA), 1.68 (m, 4H, Hc, Hc'), 2.31-2.44 (m, 4H, Hb, Hb'), 2.85 (t, 2H, Hf), 2.99-3.09 (q, CH$_2$ TEA), 3.62 (t, 2H, Hg), 3.85-3.91 (m, 4H, Hd, Hd'), 3.96 (s, 8H, Ha-Ha'), 6.11 (s, 1H, H$_g$), 6.67 (d, 2H, H$_h$). $^{31}$P NMR (200 MHz, CDCl$_3$) δ (in ppm): 0.865. MS (EI): m/z 588 (M–H)$^-$.

VI-4 Synthesis of {3-[1'-(3'-hydroxypropyl)ferrocenyl]propyl}[2-(3-pyrrolyl)ethyl]phosphate diester (Compound IIb.1)

The intermediate compound 4 obtained above was coevaporated 3 times in anhydrous THF (3×2.5 ml), then taken up in 1 ml of THF and conditioned under argon. 140 µl (0.143 mmol) of a 1M solution of TBAF in THF were then added to the reaction medium. After stirring for 3 hours, the solution was then concentrated under reduced pressure to a final volume of 0.5 ml. This crude reaction product was purified directly by chromatography on silica gel (prior neutralization with TEA) with a gradient of methanol in dichloromethane, in order to obtain a pure product in the form of an orange oil (0.013 g, 39% yield).

$^1$H NMR (200 MHz, CDCl$_3$) δ (in ppm): 1.28-1.35 (m, 9H, CH$_3$ TEA), 1.81-1.83 (m, 4H, Hc, Hc'), 2.37-2.45 (m, 4H, Hb, Hb'), 2.88 (t, 2H, Hf), 3.66 (t, 2H, Hd'), 2.92-3.06 (q, 6H, CH$_2$ TEA), 3.91-3.94 (m, 4H, Hd, He), 4.01 (s, 8H, Ha-Ha'), 6.08 (s, 1H, Hg), 6.68 (b, 2H, Hh). $^{31}$P NMR (200 MHz, CDCl$_3$) δ (in ppm): 0.43 ppm. (ESI) MS m/z: 474.1 (M–H)$^-$.

VII— Monomer (IIIa.1)

This monomer is obtained from the monomer IIa.2.

VII.1 Synthesis of Compound IIa.2:

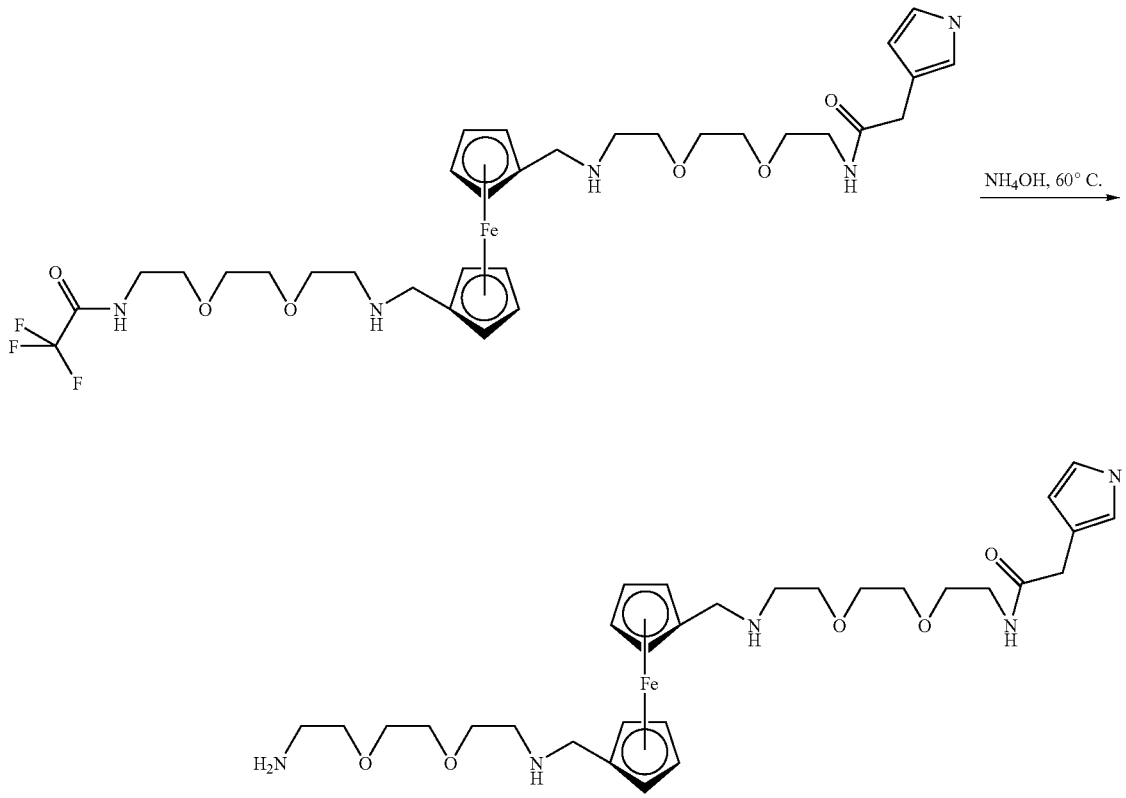

VII.2 Grafting of an oligonucleotide or of a peptide to the monomer IIa.2:

1st stage: Grafting of an activated ester to the monomer IIa.2

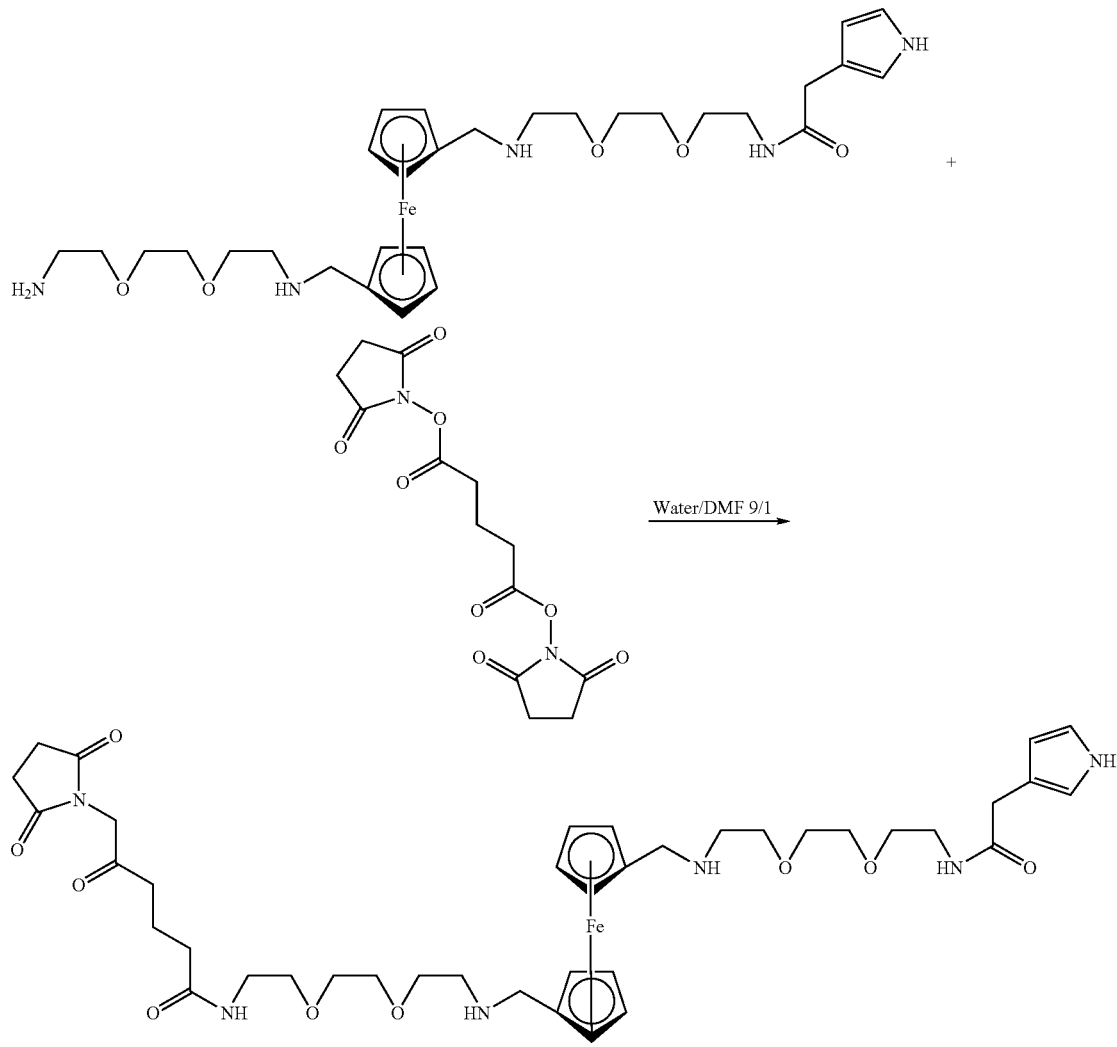

The monomer IIa.2 (1 eq.) is dissolved in water. DiSuccinimidyl Glutarate (200 eq.) is dissolved in the minimum amount of DMF, such that the final proportion of DMF does not exceed 10%. The reaction is allowed to take place at 37° C. for 2 h with stirring. Chromatography is then carried out on a reverse phase silica column, elution being carried out with a water/acetone mixture. The desired product, which can be identified by its yellow color, is recovered. The acetone is evaporated.

$2^{nd}$ stage: Grafting of the activated ester monomer to a peptide or oligonucleotide 1 eq. of peptide or oligonucleotide carrying one or more amine functional groups is added. For the oligonucleotides, it is possible to create an amine functional group at the chain end by attachment of a hexylamine. For the peptides, there is an amine in the N-terminal position and it is optionally possible to add a lysine tag which makes it possible to have primary amine functional groups on the side chains.

Coupling is allowed to take place at 37° C. for 1 h with stirring and then the conjugate can be purified by HPLC.

B. Electrochemical Characterizations and Biological Applications:

Reference will be made to the appended FIGS. 1 to 11.

FIG. 1: Reading, at 100 mV/s, in sodium acetate/acetic acid 10 mM, $LiClO_4$ 0.2M, pH 4.2 (solid left-hand line) and at pH=7 (dotted right-hand line), a layer of homopolymer obtained with the monomer (Ic.1) 30 mM, deposited at 0.60 V with a charge of 21.6 $mC/cm^2$ in sodium acetate/acetic acid 10 mM, $LiClO_4$ 0.2M, pH=4.2

Figure 2:
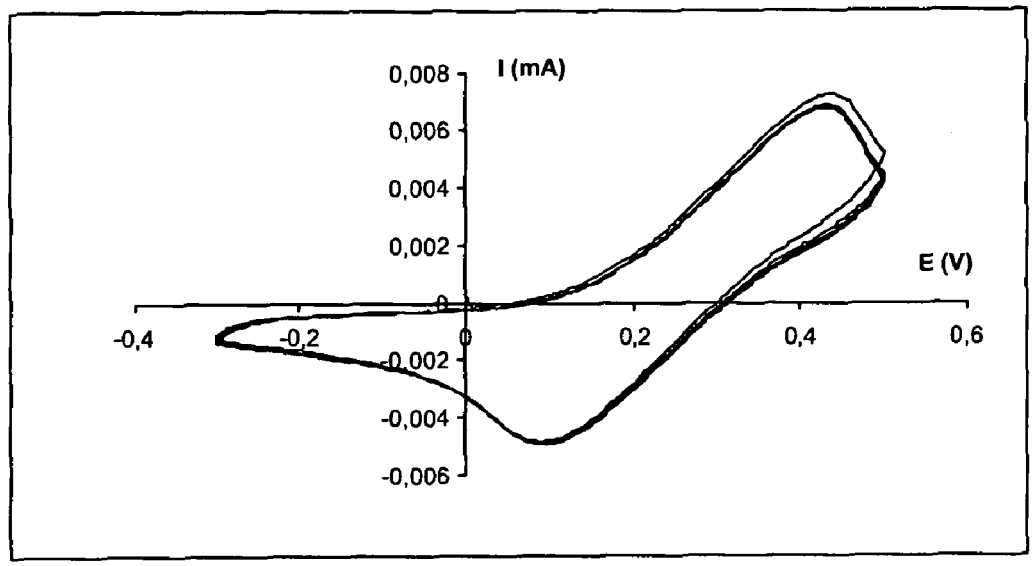

FIG. 2: Reading, at 200 mV/s, in sodium acetate/acetic acid 10 mM, $LiClO_4$ 0.2M, Tween 0.05%, pH=4.2, a layer of homopolymer obtained with the monomer (IIa.1) 100 mM, deposited at 0.65 V with a charge of 360 $mC/cm^2$ in sodium acetate/acetic acid 10 mM, pH=4.2, NaCl 0.5M, Tween 0.05%

Figure 3:
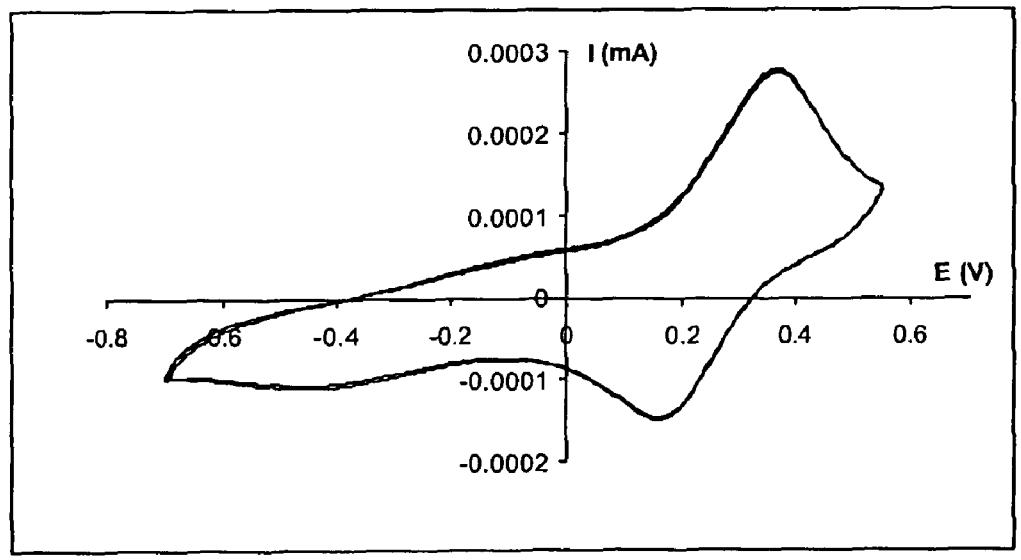

FIG. 3: Reading, at 100 mV/s, in sodium acetate/acetic acid 10 mM, pH=4.2, $LiClO_4$ 0.2M, a layer of pyrrole-3-ethanol 50 mM, monomer (IIa.1) 20 mM copolymer, deposited at 0.65 V with a charge of 21.6 mC/cm² in sodium acetate/acetic acid 10 mM, pH=4.2, LiClO₄ 0.2M FIG. 4: Reading, at 200 mV/s, in sodium acetate/acetic acid 10 mM, pH=4.2, NaCl 0.5M, a layer of pyrrole-3-ethanol 50 mM, monomer (IIa.1) 20 mM copolymer, deposited at 0.65 V FIG. 5: Reading, at 200 mV/s, in MICAM buffer, a layer of pyrrole-3-ethanol 50 mM, monomer (IIa.1) 20 mM copolymer, deposited at 0.65 V with a charge of 3.6 mC/cm² in sodium acetate/acetic acid 10 mM, pH=4.2, NaCl 0.5M FIG. 6: Reading, at 200 mV/s, in sodium acetate/acetic acid 10 mM, pH=4.2, NaCl 0.5M, Tween 0.05%, a layer of homopolymer (IIa.2), deposited at 0.65 V with a charge of 28.8 mC/cm² in sodium acetate/acetic acid 10 mM, pH=4.2, NaCl 0.5M, Tween 0.05%

Figure 7:
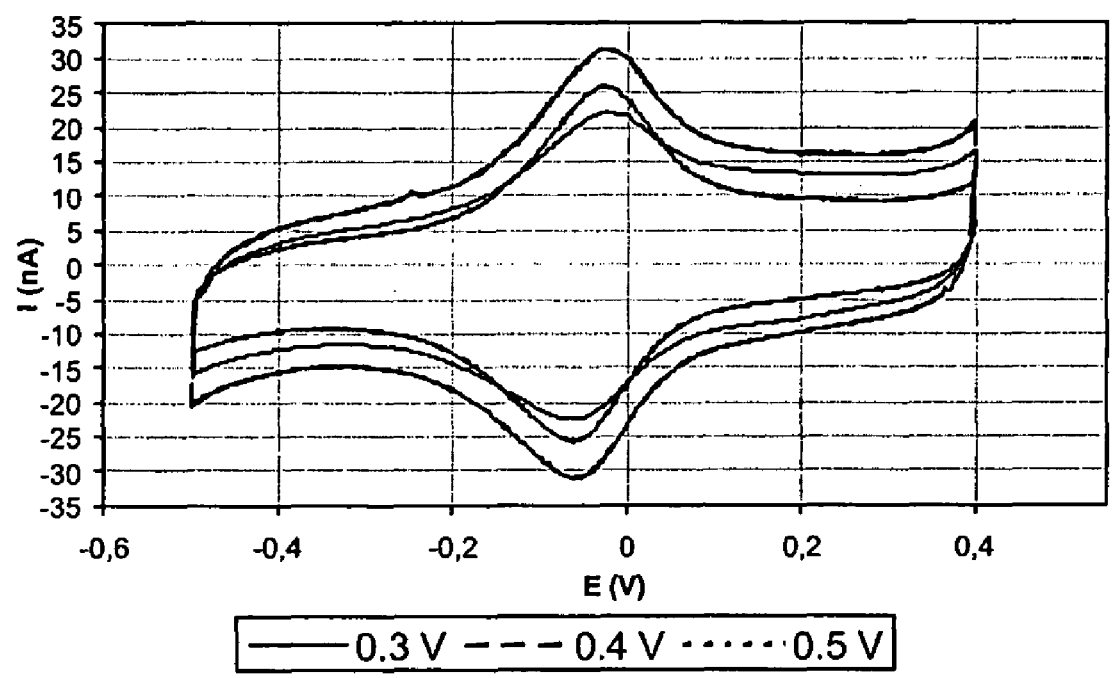

FIG. 7: Reading, at 100 mV/s, in acetic acid/sodium acetate buffer, 0.2M LiClO₄, pH=4.2, a layer of homopolymer (IIb.1), deposited at 2 mM at 3 different potentials, 0.3 V, 0.4 V and 0.5 V/FeCp₂/FeCp₂+, and at a constant charge of 10.8 mC/cm², in acetic acid/sodium acetate buffer, 0.2M LiClO₄, pH=4.2

Figure 8:
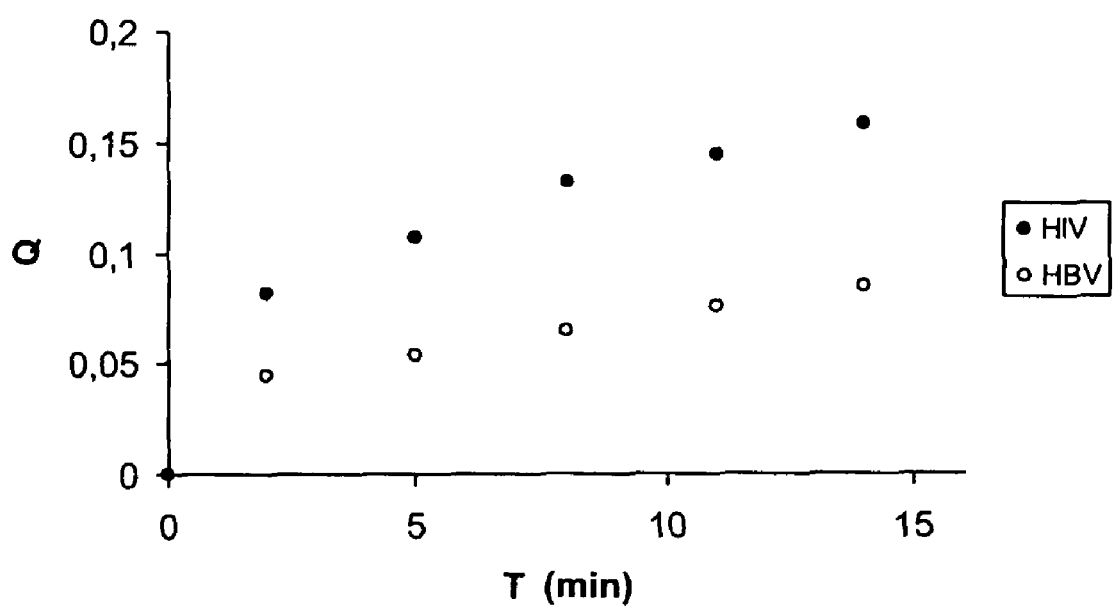

FIG. 8: Change in $Q=(I°-I)/I°$ as a function of time, where I° is the intensity of oxidation of the ferrocene at t=1 min after addition of the complementary sequence and I is the intensity at time t=x min after addition of the complementary sequence. A layer of copolymer of monomer (Ia.1) is involved.

Figure 9:
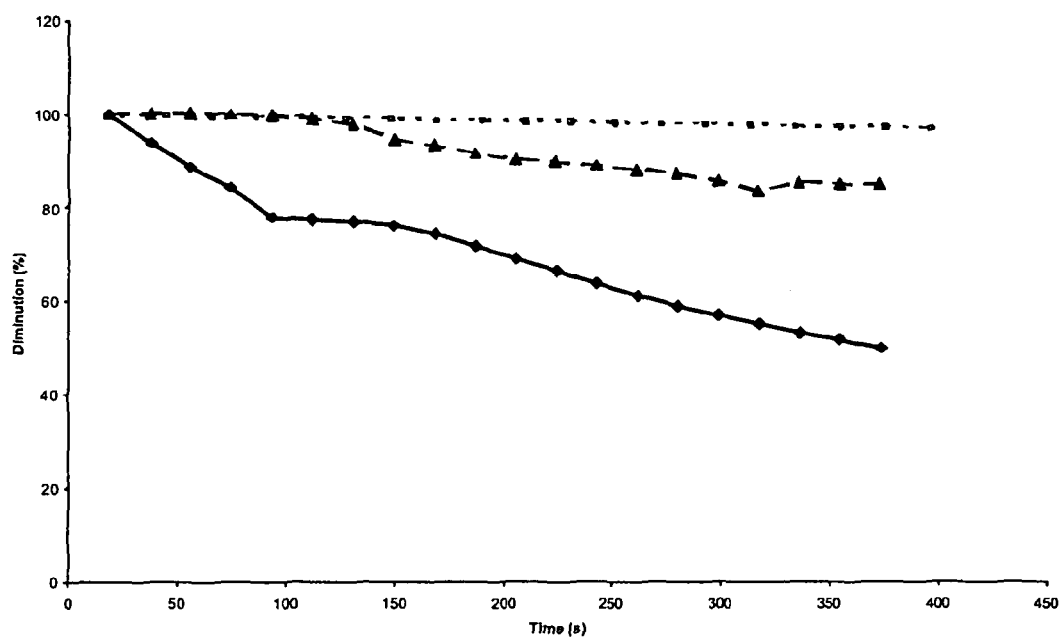

FIG. 9: Percentage of reduction in the current intensity at the oxidation peak of the ferrocene as a function of time; (■) control (polymer prepared with the monomer Ib.1 and pyrrole-3-ethanol)+addition of the HBV complementary target; (▲)+addition of the HIV noncomplementary target; (♦)+addition of the HBV complementary target.

Figure 10:
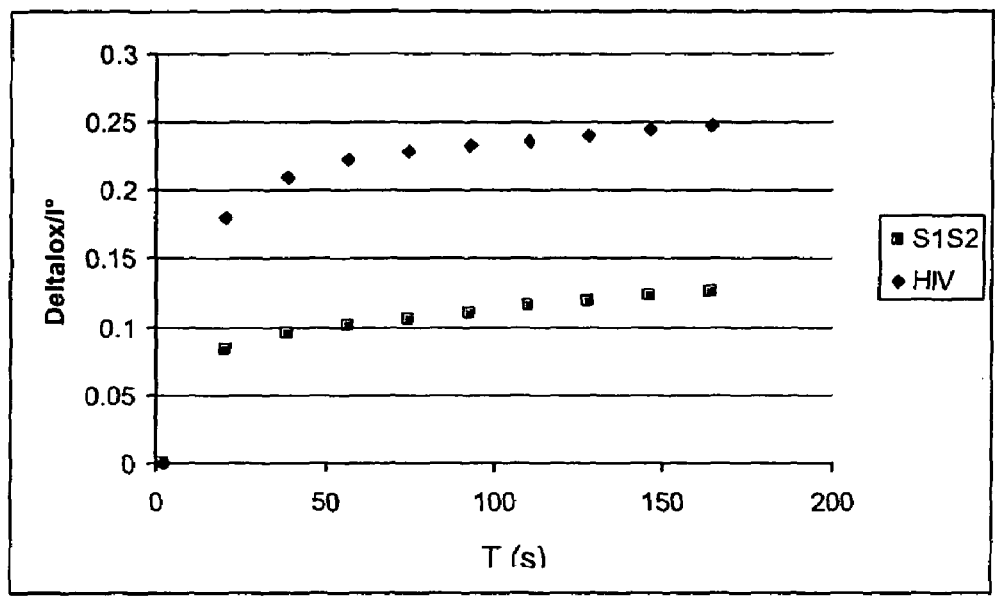

FIG. 10: Percentage of reduction in the oxidation intensity of the ferrocene during hybridization when an HIV target is added. The readings are carried out at 100 mV/s, in sodium acetate/acetic acid 10 mM, LiClO₄ 0.2M, pH=4.2, Tween 0.005% and salmon sperm DNA 10 μg/ml. It is a question of a layer of copolymer of the monomer (Ic.1) 30 mM and of pyrroles-oligonucleotides 12.5 μM (respectively py-SEQ ID No. 1 12.5 μM and [py-SEQ ID No. 2 6.25 μM+py-SEQ ID No. 3 6.25 μM]), deposited at 0.60 V with a charge of 21.6 mC/cm² in sodium acetate/acetic acid 10 mM, LiClO₄ 0.2M, pH=4.2.

Delta $Iox/I°$=[(intensity of oxidation of the ferrocene at $t$=1 min after introduction of the target)−(intensity of oxidation of ferrocene at time $t$ after introduction of the target)]/(intensity of oxidation of the ferrocene at $t$=1 min after introduction of the target).

Figure 11:
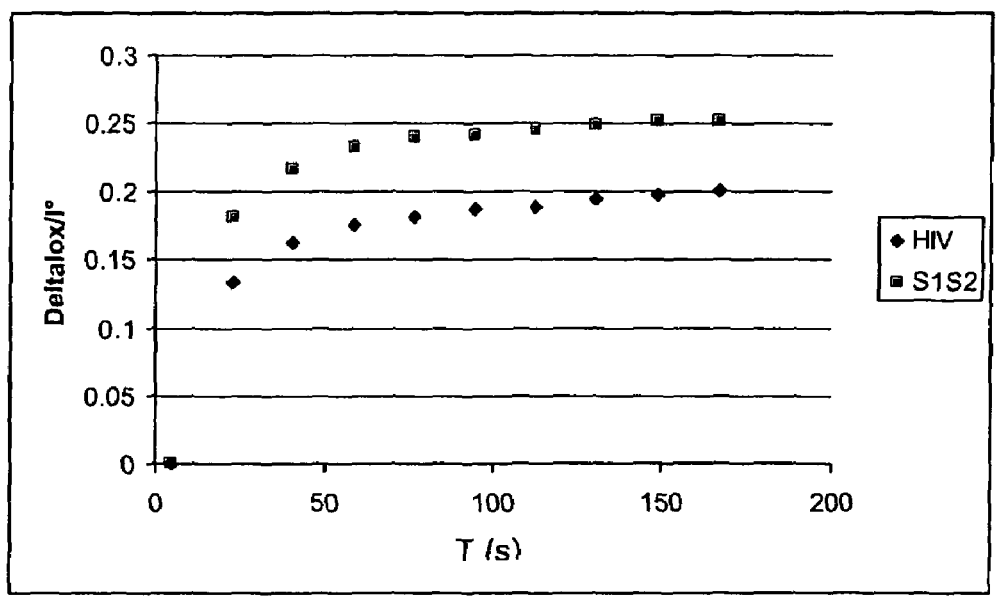

FIG. 11: Percentage of reduction in the oxidation intensity of the ferrocene during hybridization when an HBV target is added. The readings are carried out at 100 mV/s, in sodium acetate/acetic acid 10 mM, LiClO₄ 0.2M, pH=4.2, Tween 0.005% and salmon sperm DNA 10 μg/mL. It is a question of a layer of copolymer of the monomer (Ic.1) 30 mM and of pyrroles-oligonucleotides 12.5 μM (respectively py-SEQ ID No. 1 12.5 μM and [py-SEQ ID No. 2 6.25 μM+py-SEQ ID No. 3 6.25 μM]), deposited at 0.60 V with a charge of 21.6 mC/cm² in sodium acetate/acetic acid 10 mM, LiClO₄ 0.2M, pH=4.2.

Equipment:

The electrochemical studies were carried out on a VMP2 potentiostat manufactured by Bio-Logic Science Instruments SA (Claix, France). It is equipped with three channels, with a low current board and with a connector suitable for chips of ApiT8 type (LETI, Grenoble, France). This potentiostat is under the control of EC Lab version V8.32 Electrochemistry Software. Chips composed of a network of electrodes, on a conductive support, connected to spots, a reference electrode and a counterelectrode were used. An example of a process for the manufacture of these chips is described in the following paper: Cosnier, B. P., Marquette, C. and Blum, L., J. Am. Chem. Soc., 2005, 127, 18328-18332.

During the electrochemical characterizations of the monomers, the readings were carried out with a buffer already used in the detection of biological interactions. The MICAM oligonucleotide hybridization buffer (Apibio, Grenoble, France) was used. The latter buffer comprises: phosphate buffer 9.5 mM, NaCl 0.515M, KCl 2.6 mM, Tween 0.048%, Denhardt 1×, salmon sperm DNA 10 μg/mL.

I—Polymer Resulting from the Monomer (Ia.1) or from the Monomer (Ib.1)

I.a—The homopolymer was deposited from the monomer (Ia.1) at 0.60 V, with a charge of 61.2 mC/cm², at a concentration of 50 mM in a buffer consisting of sodium acetate/acetic acid 10 mM, pH 4.2, LiClO₄ 0.2M, on an electrode chip. Here again, when the reading is carried out of the layer formed in this same buffer, the oxidation and the reduction of the ferrocene are clearly seen. A stable signal is also observed in MICAM hybridization buffer.

I.b—A layer of copolymer with the monomer (Ib.1) and pyrrole-3-ethanol was also produced.

The following formulation is used: 50 mM of pyrrole-3-ethanol and 20 mM of monomer (Ib.1). The depositions are carried out at 0.60 V with a charge of 21.6 mC/cm² in buffer consisting of sodium acetate/acetic acid 10 mM, pH 4.2, LiClO₄ 0.2M.

Here again, the voltammogram obtained at 200 mV/s in the deposition buffer clearly shows the reduction and the oxidation of the ferrocene.

II—Polymer Resulting from the Monomer (Ic.1)

A homopolymer was deposited from the monomer (Ic.1) at 0.6 V with a charge of 21.6 mC/cm² in sodium acetate/acetic acid 10 mM, pH=4.2, LiClO₄ 0.2M, on an electrode chip. Another deposition was carried out under the same conditions but at a pH=7.

The voltammograms of the polymers formed are presented in FIG. 1 and reveal a major electrochemical response of the ferrocene. At pH=7, the electrochemical signal is greater, which opens up advantageous prospects for the electrochemical detection of biological interactions at physiological pH.

III—Polymer Resulting from the Monomer IIa.1

III.a—A homopolymer was deposited from the monomer (IIa.1) (50 mM) at 0.65 V with a charge of 360 mC/cm² in sodium acetate/acetic acid 10 mM, pH=4.2, LiClO₄ 0.2M, Tween 0.05%, on an electrode chip. The voltammogram of the polymer formed, in this same buffer, is presented in FIG. 2 and reveals the oxidation and the reduction of the ferrocene. The voltammogram obtained is rather asymmetric for scan rates of greater than 50 mV/s, which reflects the fact that the layer of polymer obtained is sterically constrained and thus that the electron exchanges take place less easily.

III.b—A layer of copolymer with the monomer (IIa.1) and pyrrole-3-ethanol was also produced.

The advantage of preparing a copolymer lies in the fact that it will make it possible, through the pyrrole-3-ethanols, to space out the positive charges on the surface of the layer. A concentration of 50 mM of pyrrole-3-ethanol and of 20 mM of monomer (IIa.1) is used to carry out each deposition on an electrode chip. Two deposition buffers gave good results:

the buffer consisting of sodium acetate/acetic acid 10 mM, pH 4.2, NaCl 0.5M, deposition at 0.65 V with a charge of 21.6 mC/cm$^2$, the buffer consisting of sodium acetate/acetic acid 10 mM, pH 4.2, LiClO$_4$ 0.2M, deposition at 0.65 V with a charge of 3.6 mC/cm$^2$.

Figure 4:
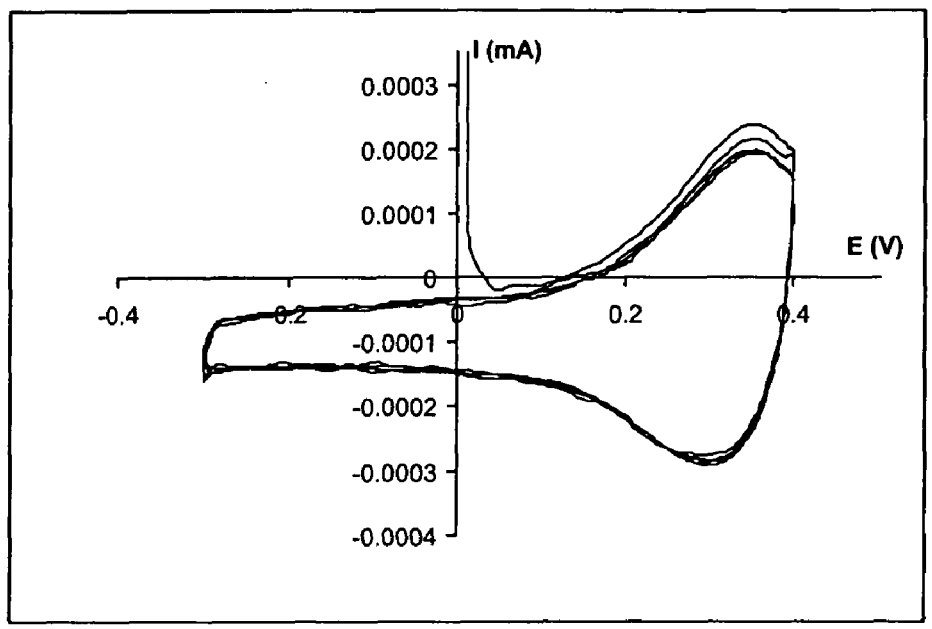
Figure 5:
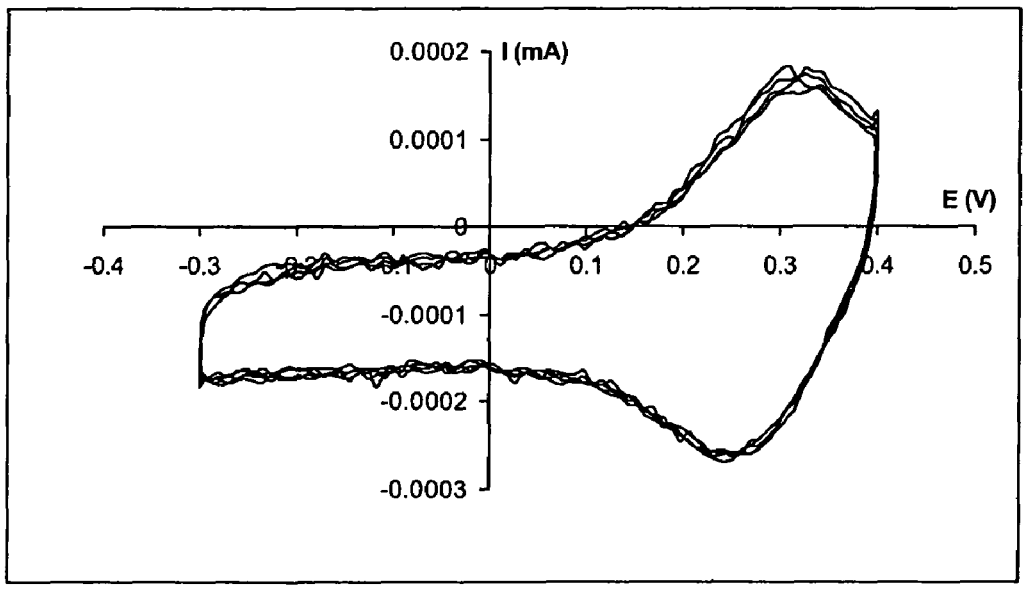

The voltammograms obtained with these buffers are given in FIG. 3, (NaCl 0.5M, and scan rate=100 mV/s) and FIG. 4 (LiClO$_4$ 0.2M, scan rate=200 mV/s) (Apibio, Grenoble, France). Stability of the signal is also observed using the MICAM hybridization buffer (Apibio, Grenoble, France), as is shown by the voltammogram given in FIG. 5 obtained for a scan rate of 200 mV/s, with the copolymer deposited in buffer consisting of sodium acetate/acetic acid 10 mM, pH 4.2, LiClO$_4$ 0.2M.

IV—Polymer Resulting from the Monomer (IIa.2)

Figure 6:
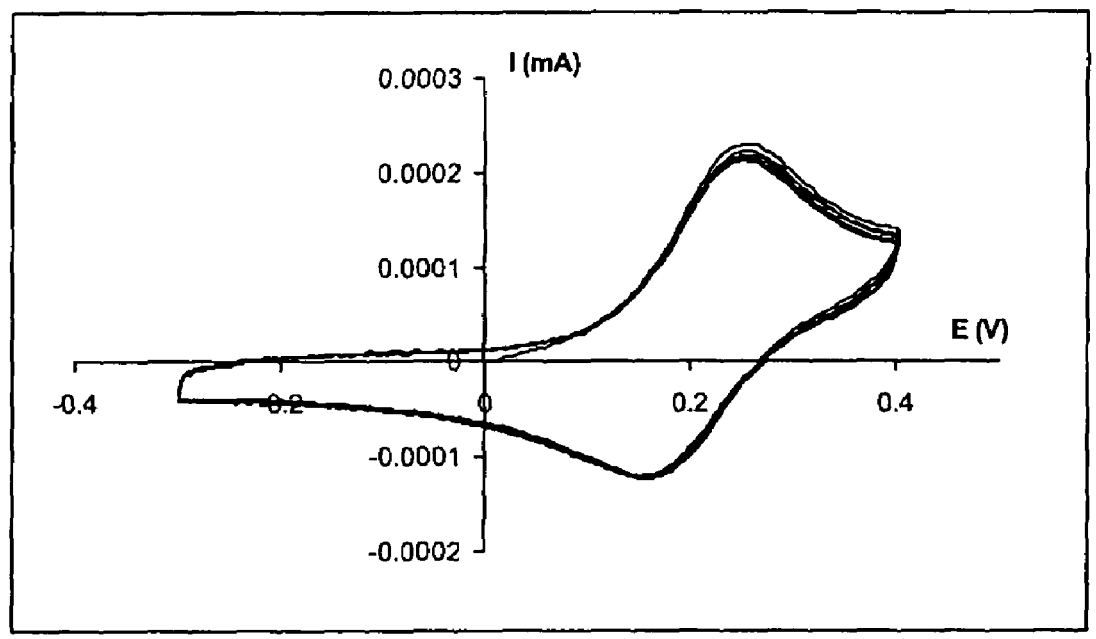

IV.a—A homopolymer was deposited from the monomer (IIa.2) at 0.65 V with a charge of 28.8 mC/cm$^2$ at a concentration of 10 mM in a buffer consisting of sodium acetate/acetic acid 10 mM, pH=4.2, NaCl 0.5M, Tween 0.05%, on an electrode chip. When the reading is carried out of the layer formed in this same buffer, the oxidation and the reduction of the ferrocene are clearly seen, as illustrated in FIG. 6.

IV.b—A layer of copolymer is formed at 0.65 V with a charge of 90 mC/cm$^2$ in sodium acetate/acetic acid 10 mM, pH=4.2, NaCl 0.5M, Tween 0.05%, from 50 mM of pyrrole-3-ethanol and 10 mM of monomer (IIa.2). The depositions are carried out in buffer consisting of sodium acetate/acetic acid 10 mM, pH 4.2, NaCl 0.5M, Tween 0.05%.

Here again, a reading at 200 mV/s in the deposition buffer reveals the oxidation and the reduction of the ferrocene.

V—Polymer Resulting from the Monomer (IIb.1)

The monomer was electropolymerized at a concentration of 2 mM in a buffer (referred to as PB for Polymerization Buffer) consisting of acetic acid/sodium acetate, LiClO$_4$ 0.2M, pH=4.2. 20 µL of solution were deposited on the spot region of the chip.

Electropolymerization was carried out by chronoamperometry at 3 different potentials, i.e. 0.3 V, 0.4 V and 0.5 V/FeCp$_2$/FeCp$_2$+, and at a constant charge of 10.8 mC/cm$^2$ (FIG. 7). After polymerization, the spots were washed successively with PB buffer, then 3 times in PB+0.05% Tween buffer and, finally, with PB buffer, for the purpose of removing the entities adsorbed on the surface of the electrodes. For the cyclic voltametry measurements, 30 µL of PB buffer were used as electrolytic solution and the cyclovoltammograms were recorded between −0.5 V and 0.4 V, at a scan rate of 0.1 V/s. The analyses clearly show the presence of the polymer on the surface of the spots and the good response of the ferrocene to oxidation and then to reduction.

Analysis by cyclic voltametry of the polymer on a carbon chip (Eox of the Fc=−0.02 V; Ered of the Fc=−0.06 V).

VI—Electroactive Probes from the Monomer Ia.1

VI.a—Immobilization of the Biological Ligand

Use was made of 22-mer oligonucleotide sequences functionalized by a pyrrole on their 5'-phosphorylated end. One of the sequences results from the HIV virus (SEQ ID No. 1). The others result from the HBV-105C virus (SEQ ID No. 2 and SEQ ID No. 3). The grafting of the pyrrole is carried out by coupling 3-methyl-N-hydroxysuccinimide-pyrrole to an oligonucleotide modified in the 5' position by a hexylamine.

A copolymer was obtained from 50 mM of monomer pyrrole-3-ethanol, 15 mM of the monomer Ia.1 and 12.5 µM of monomer pyrrole-oligonucleotide in 20 µL of sodium acetate/acetic acid 10 mM, LiClO$_4$ 0.2M, pH 4.2, by applying a potential of 0.55 V and a charge of 21.6 mC/cm$^2$. On an electrode chip, one electrode is targeted with the oligonucleotide resulting from the HIV virus (SEQ ID No. 1) and another with the two oligonucleotides resulting from the HBV virus (SEQ ID No. 2 and SEQ ID No. 3, each at 6.25 µM).

VI.b—Hybridization

The hybridization buffer comprises sodium acetate/acetic acid 10 mM, LiClO$_4$ 0.2M, pH=4.2, 0.005% Tween 20 and salmon sperm DNA 10 µg/ml.

The chip is saturated in this buffer for 10 minutes. 100 µM of sequence complementary to the sequence SEQ ID No. 1 (SEQ ID No. 4) are then added. The sequence SEQ ID No. 4 is a 33-mer. Cyclic voltametry cycles are then started at 100 mV/s between −0.5 and 0.5 V, continuously for 20 minutes.

FIG. 8 represents the change in Q=(I°−I)/I° as a function of time. The slopes at the start of these curves are calculated and make it possible to easily distinguish the spot comprising the sequence complementary to SEQ ID No. 1 (HIV) as its slope value is greater.

VII—Electroactive Probes from the Monomer Ib.1

VII.a—Immobilization of the Biological Ligand (HBV Probe)

The HBV capture probe oligonucleotide (SEQ ID No. 3) modified in the 5' position by a pyrrole (HBV-105C) is immobilized on the spots of the carbon chip by copolymerization with the compound Ib.1 and pyrrole-3-ethanol. 30 µL of a solution comprising 50 mM of pyrrole-3-ethanol, 3 mM of the compound Ib.1 and 12.5 µM of ODN (5'-pyrrole) in a buffer consisting of LiClO$_4$ 0.2M, sodium acetate 10 mM, Tween 0.025%, pH 4.2, are deposited on the spot region. A charge to be achieved of 22 mC/cm$^2$ is then imposed on the spots to be targeted, at a fixed potential of 0.65 V. The surface of the spots is then carefully washed with the same buffer and then in Milli-Q water, before incubating in the measuring buffer until the oxidation/reduction signal of the polymer layer has stabilized.

VII.b—Monitoring of the hybridization with the complementary target (SEQ ID No. 5, representing the HBV DNA target with a length of 86 bases) and the noncomplementary target (SEQ ID No. 4, representing the HIV target with a length of 33 bases).

The hybridization reaction is monitored over time by measuring the electrochemical response of the electrodeposited polymer films. 30 µL of target DNA (HBV or HIV) at a concentration of 100 nM in MICAM buffer are initially deposited on the spot region of the chip and monitoring is carried out by measuring the variation in the current intensity at the oxidation peak of the ferrocene. The blank is produced on a polymer spot not comprising capture oligonucleotide. The stability of the current over time is thus confirmed. The results illustrated in FIG. 9 reveal a marked decrease in the current intensity in the case of the positive spots. The suppression is significant and confirms the satisfactory sensitivity of the polymer films with regard to hybridization.

VIII—Electroactive Probes from the Monomer (Ic.1)

VIII.a—Immobilization of the Biological Ligand

Monomer (Ic.1) is copolymerized, at 0.60 V and 21.6 mC/cm$^2$, with pyrrole monomers functionalized by oligonucleotides (SEQ ID No. 1, SEQ ID No. 2, SEQ ID No. 3; supplied by Biomérieux Polytech). The concentrations of the monomers are 15 mM and 3.75 μM respectively. Deposition is carried out in buffer consisting of acetic acid/sodium acetate 10 mM, LiClO$_4$ 0.2M, pH=4.2.

Identical depositions are carried out on two chips. Each comprises two polymerized spots: one with an ODN sequence resulting from the HIV system (SEQ ID No. 1), and another with two ODN sequences resulting from the HBV system (SEQ ID No. 2 and 3). A sequence complementary (SEQ ID No. 4; 10 nM) to SEQ ID No. 1 resulting from the HIV system is added to one chip (FIG. 10). A sequence complementary (SEQ ID No. 5; 10 nM) to SEQ ID No. 2 and 3 resulting from the HBV system is added to the other chip (FIG. 11).

It is seen that, when the complementary sequence is added, the intensity of oxidation of the ferrocene decreases. This makes it possible to easily distinguish the spots on which the complementary sequences have been hybridized from the spots where hybridization has not taken place.

What is claimed is:

1. A monomer of formula (I):

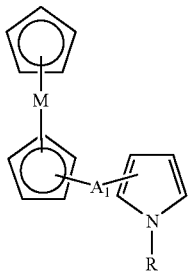

wherein:
- M is a transition metal,
- $A_1$ is a connecting arm ionizable in aqueous solution having a sequence selected from the group consisting of:
  -A2-X-A3- with:
  - X which represents $-NR^1-$, $-Y-P(O)(OR^2)-O-$ or $-N^+R^6R^7-$
  - Y which represents O or NH,
  - $A_2$ which represents $-(CH_2)_{m1}-$, $-(CH_2)_{m2}-O-[(CH_2)_2O]_{m3}-(CH_2)_2-$ or $-(CH_2)_{m4}-C(O)-NR^3-[(CH_2)_2O]_{m5}-(CH_2)_2-$,
  - $A_3$ which represents $-(CH_2)_{n1}-$, $-[(CH_2)_2O]_{n2}-(CH_2)_{n3}-$ or $-[(CH_2)_2O]_{n4}-(CH_2)_2-NR^4-C(O)-(CH_2)_{n5}-$,
  - m1 and n1 which represent, each independently of one another, an integer included within the range extending from 1 to 6; wherein, if X represents $-NR^1-$ and the groups $A_2$ and $A_3$ respectively represent $-(CH_2)_{m1}-$ and $-(CH_2)_{n1}-$, then the sum m1+n1 is included within the range extending from 2 to 6,
  - m2 and n3 which represent, each independently of one another, an integer included within the range extending from 0 to 3,
  - m3, n2, m4, n4, m5 and n5 which represent, each independently of one another, an integer included within the range extending from 0 to 6,
  - $R^1$, $R^3$ and $R^4$ which represent, each independently of one another, a hydrogen atom or a $(C_1-C_4)$alkyl group, and
  - $R^2$ which represents a hydrogen atom or a $(C_1-C_4)$ alkyl, cyanoethyl or 2-chlorophenyl group, and -$A_4$-[NH(CH$_2$)$_2$]$_n$-$A_5$- with:
- $A_4$ which represents $-(CH_2)_{p1}-$ or $-(CH_2)_{p2}-C(O)-$,
- $A_5$ which represents $-(CH_2)_{q1}-$ or $-NR^5-C(O)-(CH_2)_{q2}-$,
- n which is an integer included within the range extending from 2 to 6,
- p1, q1, p2 and q2 which represent, each independently of one another, an integer included within the range extending from 1 to 6,
- $R^5$ which represents a hydrogen atom or a $(C_1-C_4)$ alkyl group, and
- $R^6$, $R^7$ which represent, each independently of one another, a $(C_1-C_4)$alkyl group, wherein R represents a hydrogen atom or a protective group for the amine functional group.

2. The monomer as claimed in claim 1, wherein the monomer corresponds to the formula (Ia):

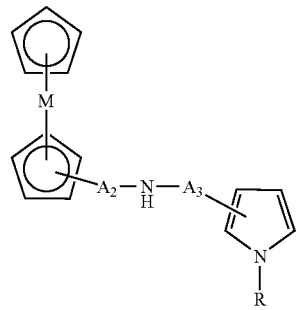

wherein at least one of the sequences $A_2$ and $A_3$ comprises a unit $-[(CH_2)_2O]_m-$ in which m represents an integer included within the range extending from 0 to 6.

3. The monomer as claimed in claim 1, wherein the monomer corresponds to the formula (Ic):

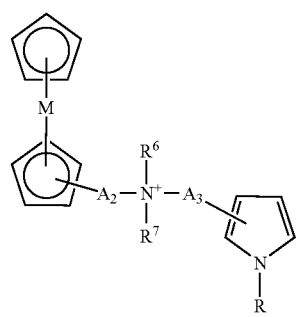

with wherein at least one of the sequences $A_2$ and $A_3$ comprises a unit $-[(CH_2)_2O]_m-$ where m represents an integer included within the range extending from 0 to 6.

4. The monomer as claimed in claim 3, wherein $R^6$ and $R^7$ respectively represent $-(CH_3)$.

5. The monomer as claimed in claim 2, wherein $A_2$ represents $-(CH_2)_{m1}-$ and $A_3$ represents $-[(CH_2)_2O]NR^4-C(O)-(CH_2)_{n5}-$.

6. The monomer as claimed in claim 5, wherein m1=1, N4=2, n5=1 and $R^4$=H.

7. The monomer as claimed in claim 1, wherein the monomer corresponds to the formula (Ib):

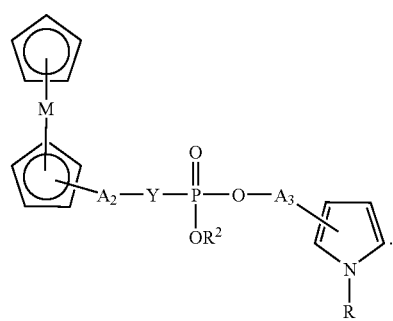

8. The monomer as claimed in claim 7, wherein Y=O.

9. The monomer as claimed in claim 7, wherein $R^2$ represents a hydrogen atom.

10. The monomer as claimed in claim 7, wherein $A_2$ and $A_3$ respectively represent —$(CH_2)_{m1}$- and —$(CH_2)_{n1}$-.

11. The monomer as claimed in claim 10, wherein m1=3 and n1=2.

12. The monomer as claimed in claim 1, wherein the bonding between the ionizable connecting arm and the pyrrole unit takes place at the 3 position of the pyrrole.

13. The monomer as claimed in claim 1, wherein M is iron.

14. The monomer as claimed in claim 1, wherein R is a hydrogen atom.

* * * * *